United States Patent
Herzog et al.

(10) Patent No.: US 11,744,880 B2
(45) Date of Patent: Sep. 5, 2023

(54) BLOOD COAGULATION FACTOR REPLACEMENT PRODUCT FOR USE IN THE TREATMENT OR PROPHYLAXIS OF BLEEDINGS

(71) Applicant: CSL Behring GmbH, Marburg (DE)

(72) Inventors: Eva Herzog, Chesterbrook, PA (US); Gerald Hochleitner, Mieming (AT); Oliver Grottke, Aachen (DE)

(73) Assignee: CSL Behring GmbH, Marburg (DE)

(*) Notice: Subject to any disclaimer, the term of this patent is extended or adjusted under 35 U.S.C. 154(b) by 598 days.

(21) Appl. No.: 16/474,803

(22) PCT Filed: Feb. 9, 2018

(86) PCT No.: PCT/EP2018/053240
§ 371 (c)(1),
(2) Date: Jun. 28, 2019

(87) PCT Pub. No.: WO2018/146235
PCT Pub. Date: Aug. 16, 2018

(65) Prior Publication Data
US 2019/0351028 A1   Nov. 21, 2019

(30) Foreign Application Priority Data
Feb. 9, 2017   (EP) ..................................... 17155420

(51) Int. Cl.
| A61K 38/36 | (2006.01) |
| A61P 7/02 | (2006.01) |
| A61K 31/727 | (2006.01) |
| A61K 38/38 | (2006.01) |
| A61K 38/48 | (2006.01) |

(52) U.S. Cl.
CPC ............ *A61K 38/36* (2013.01); *A61K 31/727* (2013.01); *A61K 38/385* (2013.01); *A61K 38/4833* (2013.01); *A61K 38/4846* (2013.01); *A61P 7/02* (2018.01); *C12Y 304/21005* (2013.01); *C12Y 304/21021* (2013.01); *C12Y 304/21022* (2013.01); *C12Y 304/21038* (2013.01)

(58) Field of Classification Search
CPC .............. A61K 38/36; A61K 38/4846; A61K 38/4833; A61K 31/727; A61K 38/385; A61K 38/48; A61K 38/00; A61K 38/38; A61K 2300/00; A61P 7/00; A61P 7/04; A61P 7/02; C12Y 304/21005; C12Y 304/21021; C12Y 304/21022; C12Y 304/21038
See application file for complete search history.

(56) References Cited

U.S. PATENT DOCUMENTS

| 4,411,794 A | 10/1983 | Schwinn et al. |
| 4,663,164 A | 5/1987 | Thomas |
| 5,407,671 A | 4/1995 | Heimburger et al. |
| 5,866,122 A | 2/1999 | Turecek et al. |
| 6,346,277 B1 | 2/2002 | Heimburger et al. |
| 2015/0258182 A1 | 9/2015 | Dockal et al. |

FOREIGN PATENT DOCUMENTS

| CN | 102459583 A | 5/2012 |
| EP | 0 056 629 A1 | 7/1982 |
| WO | WO 2010/140140 A1 | 12/2010 |
| WO | WO 2012/045569 A1 | 4/2012 |
| WO | WO 2016/198351 A1 | 12/2016 |

OTHER PUBLICATIONS

Dentali et al, "Risk factors for suboptimal efficacy of 3-factor prothrombin complex concentrates in emergency VKA anticoagulation reversal," Thromb Haemost, 112(3): 621-623, (2014).
Dickneite et al., "Characterization of the coagulation deficit in porcine dilutional coagulopathy and substitution with a prothrombin complex concentrate," Anesth Analg, 106(4): 1070-1077, (2008).
Dickneite et al., "Prothrombin complex concentrate vs fresh frozen plasma for reversal of dilutional coagulopathy in a porcine trauma model," Br J Anaesth, 102(3): 345-354, (2009).
Dusel et al., "Identification of prothrombin as a major thrombogenic agent in prothrombin complex concentrates," Blood Coagul Fibrinolysis, 15(5): 405-411, (2004).
Grottke et al., "Thrombin generation capacity of prothrombin complex concentrate in an in vitro dilutional model," PLoS One, 8(5): e64100, (2013).
Honickel et al., "Prothrombin complex concentrate reduces blood loss and enhances thrombin generation in a pig model with blunt liver injury under severe hypothermia," Thromb Haemost, 106(4): 724-733, (2011).
Honickel et al., "Co-administration of Antithrombin (AT) prevents imbalances of the coagulation system after high-dose Prothrombin complex concentrate (PCC) in a porcine polytrauma model," 60th Annual Meeting of the Society of Thrombosis and Haemostasis Research, Muenster, Germany (2016).
Josíc et al., "Manufacturing of a prothrombin complex concentrate aiming at low thrombogenicity," Thromb Res, 100(5): 433-441, (2000).

(Continued)

*Primary Examiner* — Taeyoon Kim
*Assistant Examiner* — Tiffany M Gough
(74) *Attorney, Agent, or Firm* — Finnegan, Henderson, Farabow, Garrett & Dunner, LLP

(57) ABSTRACT

The invention pertains to a blood coagulation factor replacement product for use in the treatment or prophylaxis of bleedings of patients having an acquired coagulation factor deficiency or for use in the treatment or prophylaxis of bleedings of patients having a congenital deficiency of a coagulation factor. Said product comprises at least isolated prothrombin (Factor II) and isolated Antithrombin III (ATIII), whereby the molar ratio between ATIII to Factor II is at least 1:30. By administration of said product the patient's risk for a thromboembolic complication is reduced.

16 Claims, 11 Drawing Sheets

(56) References Cited

OTHER PUBLICATIONS

Kaspereit et al., "Prothrombin complex concentrate mitigates diffuse bleeding after cardiopulmonary bypass in a porcine model," British Journal of Anaesthesia, 105(5): 576-582, (2010).
Levy et al., "Perioperative hemostatic management of patients treated with vitamin K antagonists," Anesthesiology, 109(5): 918-926, (2008).
Manning, "Fluid and Blood Resuscitation," Chapter 31, (2004).
Mitrophanov et al., "Therapeutic correction of thrombin generation in dilution-induced coagulopathy: computational analysis based on a data set of healthy subjects," J Trauma Acute Care Surg, 73(2 Suppl 1): S95-S102, (2012).
Mitrophanov et al., "A Step Toward Balance: Thrombin Generation Improvement via Procoagulant Factor and Antithrombin Supplementation," Anesth Analg, 123(3): 535-546, (2016).
Mitterlechner et al., "Prothrombin complex concentrate and recombinant prothrombin alone or in combination with recombinant factor X and FVIIa in dilutional coagulopathy: a porcine model," J Thromb Haemost, 9(4): 729-737, (2011).
Ostermann et al., "Pharmacokinetics of Beriplex P/N prothrombin complex concentrate in healthy volunteers," Thromb Haemost, 98(4): 790-797, (2007).
Pabinger et al., "Prothrombin complex concentrate (Beriplex® P/N) for emergency anticoagulation reversal: a prospective multinational clinical trial," J Thromb Haemost, 6(4): 622-631, (2008).
Riess et al., "Prothrombin complex concentrate (Octaplex) in patients requiring immediate reversal of oral anticoagulation," Thromb Res, 121(9): 9-16, (2007).
Rodgers, "Prothrombin complex concentrates in emergency bleeding disorders," Am J Hematol, 87(9): 898-902, (2012).
Spronk et al., "Assessment of thrombin generation II: Validation of the Calibrated Automated Thrombogram in platelet-poor plasma in a clinical laboratory," Thromb Haemost, 100(2): 362-364, (2008).
Tazarourte et al., "Guideline-concordant administration of prothrombin complex concentrate and vitamin K is associated with decreased mortality in patients with severe bleeding under vitamin K antagonist treatment (EPAHK study)," Crit Care, 18(2): R81, (2014).
Wiedermann et al., "Warfarin-induced bleeding complications—clinical presentation and therapeutic options," Thromb Res, 122 Suppl 2: S13-18, (2008).
"Clinical Laboratory Diagnostics: Use and Assessment of Clinical Laboratory Results," Chapter 17, edited by Lothar Thomas, (1998).
Grottke et al., "Increasing concentrations of prothrombin complex concentrate induce disseminated intravascular coagulation in a pig model of coagulopathy with blunt liver injury," Blood, 118(7):1943-1951, (2011).
Grottke et al., "Prothrombin complex concentrates in trauma and perioperative bleeding," Anesthesiology, 122(4): 923-931, (2015).
Grottke et al., "Efficacy of prothrombin complex concentrates for the emergency reversal of dabigatran-induced anticoagulation," Crit Care, 20:115, (2016).
Sørensen et al., "Clinical review: Prothrombin complex concentrates—evaluation of safety and thrombogenicity," Crit Care, 15(1):201, (2011).
International Search Report for PCT/EP2018/053240, dated Apr. 13, 2018.
Written Opinion of the International Searching Authority for PCT/EP2018/053240.
Rong et al., Biomedical Biomimetic Polymer Material, South China University of Technology Press (2010), 3 pages, including Title page, Copyright page, and p. 115.
Xudong et al., "Handbook of Drugs for Hematologic Diseases," People's Medical Publishing House (2001), 4 pages, including Title page, Copyright page, and pp. 63-64.

BLOOD COAGULATION FACTOR REPLACEMENT PRODUCT FOR USE IN THE TREATMENT OR PROPHYLAXIS OF BLEEDINGS

This application is the United States national stage entry under 35 U.S.C. § 371 of International Application No. PCT/EP2018/053240, filed on Feb. 9, 2018 and published as WO 2018/146235 A1, which claims priority to European Patent Application No. 17155420.7, filed on Feb. 9, 2017. The contents of these applications are each incorporated herein by reference in their entirety.

FIELD OF THE INVENTION

The invention pertains to a blood coagulation factor replacement product for use in the treatment or prophylaxis of bleedings of patients having an acquired coagulation factor deficiency or for use in the treatment or prophylaxis of bleedings of patients having a congenital deficiency of a coagulation factor.

BACKGROUND OF THE INVENTION

Prothrombin complex concentrates (PCCs) are recommended in preference to other treatments such as therapeutic plasma for urgent reversal of vitamin K antagonists (Tazarourte K, et al. (EPAHK study). Crit Care 2014; 18(2):R81). PCCs have been also used for many years in Europe, where their license is not restricted to vitamin K antagonist reversal—they have broad approval for "treatment and prophylaxis of bleeding in acquired deficiency of the prothrombin complex coagulation factors. PCCs contain either three or four coagulation factors (factors II, IX and X, with or without factor VII) and, depending on formulation, low doses of coagulation inhibitors such as protein C, protein S and heparin.

The mechanism of action of PCCs is important for understanding their therapeutic applications. Vitamin K antagonists such as warfarin function by reducing levels of four coagulation factors: II, VII, IX and X, with the aim of preventing thromboembolism. For patients with life-threatening bleeding, rapid replacement of these coagulation factors is required, and PCCs serve as a concentrated source of the required coagulation factors. Three-factor as well as four-factor PCCs have been explored for vitamin K antagonist reversal. However, due to the absence of factor VII, it appears that three-factor PCCs are less suitable than four-factor PCCs for patients with an international normalized ratio (INR)>3.7 (Dentali F, et al. Thromb Haemost 2014; 112: 621-23).

In trauma and perioperative bleeding, patients present with a variety of coagulopathies. PCCs increase thrombin generation by ensuring adequate levels of the key coagulation factors—notably factor II (prothrombin), whose conversion to thrombin is facilitated by activated factor X and activated factor V. Treatment with PCCs may potentially be effective in facilitating hemostasis in trauma and perioperative bleeding. There is also evidence for the use of PCCs to reverse the anticoagulant effect of direct FIIa or FXa inhibitors (DOACs) in humans.

For the treatment of DOAC-induced anticoagulation, PCCs do not act as specific reversal agents. Instead, they raise levels of the vitamin K-dependent coagulation factors.

The potential risk of thromboembolic complications necessitates a cautious approach when using PCCs in trauma, perioperative bleeding. In these settings—unlike vitamin K antagonist reversal—levels of coagulation inhibitors as well as procoagulants are often decreased. The goal is to enhance thrombin generation and/or fibrin formation, to promote clot formation at the site(s) of hemorrhage but not systemically throughout the circulatory system. Depending on formulation, PCCs contain low doses of coagulation inhibitors such as protein C, protein S and heparin. However, this does not eliminate the risk of thromboembolic complications (Grottke O, et al. Blood 2011; 118:1943-51; Levy J H, et al. Anesthesiology 2008; 109:918-26; Mitterlechner T, et al. J Thromb Haemost 2011; 9:729-37; Hanker Dusel C, et al. Blood Coagul Fibrinolysis 2004; 15:405-11; Rodgers G M. Am J Hematol 2012; 87:898-902; Dickneite G, et al. Anesth Analg 2008; 106:1070-7; Dickneite G, Pragst I. Br J Anaesth 2009; 102:345-54; Kaspereit F, et al. Br J Anaesth 2010; 105:576-82).

A number of preclinical studies have investigated the use of PCC in the treatment of trauma-induced bleeding. All studies indicate that PCC can be effective in restoring hemostasis, but the evidence also shows that PCCs can cause procoagulant effects, such as thromboembolic complications and disseminated intravascular coagulation (DIC) in animal models, so risk vs benefit considerations should always be considered (Grottke O, et al. Blood 2011; 118:1943-51).

PCCs have been associated with a possible risk of thromboembolic complications, in clinical practice some years ago and in animal studies (Levy J H, et al. Anesthesiology 2008; 109:918-26; Mitterlechner T, et al. J Thromb Haemost 2011; 9:729-37; Hanker Dusel C, et al. Blood Coagul Fibrinolysis 2004; 15:405-11). In the late 1990s, activated factors were removed from most PCCs with the aim of improving safety. Factor II (prothrombin) has been identified as the key determinant of thrombogenicity in today's PCCs, leading to a suggestion that they should be labelled according to the content of factor II instead of factor IX (Hanker Dusel C, et al. Blood Coagul Fibrinolysis 2004; 15:405-11). Circulating levels of anticoagulants are also likely to affect patients' risk of thromboembolic complications. PCCs are sometimes described in the literature as being balanced (Kaspereit F, et al. Br J Anaesth 2010; 105:576-82; Josic D, et al. Thromb Res 2000; 100:433-41; Ostermann H, et al. Thromb Haemost 2007; 98:790-7; Pabinger I, et al. J Thromb Haemost 2008; 6:622-31; Riess H B, et al. Thromb Res 2007; 121:9-16; Wiedermann C J, Stockner I. Thromb Res 2008; 122 Suppl 2:S13-8). It is important to clarify that, although these products may be balanced regarding the ratios of coagulation factors II, VII, IX and X, they are not balanced regarding levels of procoagulants versus inhibitors. PCCs are highly potent thrombin generating drugs: a study in trauma patients has shown that they elicit a significant increase in endogenous thrombin potential for 3-4 days, a period that is consistent with the 60-72 hour half-life of factor II.

Pharmacovigilance data indicate that the risk of thromboembolic complications with PCCs may be low, but it must be remembered that the predominant setting from which these data are derived is vitamin K antagonist reversal.

It has been suggested only low doses of PCCs should be administered, and to use a theragnostic approach for dose titration as required (Honickel M, et al. Thromb Haemost 2011; 106:724-33). Additionally, levels of antithrombin (the most potent inhibitor of the activated forms of the four coagulation factors contained in PCCs) may be measured, although there is currently no evidence to support best practice regarding threshold levels or how to manage patients with a deficiency. Finally, for patients believed to be at risk of thromboembolic complications (e.g. individuals with a history of thromboembolic events), close monitoring may be appropriate. Careful consideration of the above steps would result in a notably different approach to using PCCs compared with established practice for emergency vitamin K antagonist reversal.

There is a medical need for a safe and effective procoagulant drug providing effective hemostatic control and bleeding prophylaxis in patients, in particular on anticoagulation therapy, in case of major bleeding or requirement for urgent surgery.

Further, there is medical need for a safe and effective procoagulant drug providing rapid hemostatic control in perioperative bleeding situations.

The respective intervention should present a maximum benefit risk balance, i.e. provide maximum prohemostatic properties while eliciting minimal potential thrombogenicity.

SUMMARY OF THE INVENTION

A first object of present invention was to provide an improved blood coagulation factor replacement product, associated with a reduced patient's risk for a thromboembolic complication following administration of said product, i.e. having an improved safety profile.

According to a second object, said treatment should allow for effective hemostatic control and bleeding prophylaxis in patients, i.e. having in addition to an improved safety profile adequate efficacy or even improved efficacy.

According to a third object, administration of said safe and effective blood coagulation factor replacement product should allow for providing effective hemostatic control and bleeding prophylaxis in patients, in particular on anticoagulation therapy, in case of major bleeding or requirement for urgent surgery.

According to a further object, administration of said safe and effective blood coagulation factor replacement product should allow for providing rapid hemostatic control in perioperative bleeding situations.

According to a further object, administration of said safe and effective blood coagulation factor replacement product should allow for a maximum benefit risk balance, i.e. provide maximum prohemostatic properties while eliciting minimal potential thrombogenicity.

It has been surprisingly found by the inventors that either administration of a blood coagulation factor replacement product comprising at least prothrombin (Factor II) and Antithrombin III (ATIII) or co-administration of a blood coagulation factor replacement product comprising at least prothrombin (Factor II) together with antithrombin III to a patient minimizes or even inhibits a blood coagulation factor replacement product's thrombogenic potential while maintaining adequate efficacy or even improved efficacy as long as the molar ratio between ATIII to Factor II is at least 1:30. Thus, the patient's risk for a thromboembolic complication is reduced. Preferably, prothrombotic effects are prevented.

The invention further demonstrates that said molar ratio between ATIII to Factor II according to a further aspect can prevent excessive thrombin generation above normal/physiological levels.

In a first aspect, the present invention relates to a blood coagulation factor replacement product
(i) for use in the treatment or prophylaxis of bleedings of patients having an acquired coagulation factor deficiency or
(ii) for use in the treatment or prophylaxis of bleedings of patients having a congenital deficiency of a coagulation factor;
said product comprising at least isolated prothrombin (Factor II) and isolated Antithrombin III (ATIII), wherein the molar ratio between ATIII to Factor II is at least 1:30; and wherein by administration of said product the patient's risk for a thromboembolic complication is reduced.

In a second aspect, the present invention pertains to a combination of a Prothrombin complex concentrate (PCC) and Antithrombin III (ATIII)
(i) for use in the treatment or prophylaxis of bleedings of patients having an acquired coagulation factor deficiency or
(ii) for use in the treatment or prophylaxis of bleedings of patients having a congenital deficiency of a coagulation factor,
the PCC comprising at least prothrombin (Factor II), Factor IX, Factor X and optionally Factor VII; and
wherein by administration of said combination the patient's risk for a thromboembolic complication is reduced.

In a third aspect, the present invention pertains to a combination therapy comprising administration of a Prothrombin complex concentrate (PCC) and co-administration of Antithrombin III (ATIII)
(i) for treatment or prophylaxis of bleedings of patients having an acquired coagulation factor deficiency or
(ii) for treatment or prophylaxis of bleedings of patients having a congenital deficiency of a coagulation factor,
the PCC comprising at least prothrombin (Factor II), Factor IX, Factor X and optionally Factor VII; and
wherein by administration of said combination the patient's risk for a thromboembolic complication is reduced.

According to a fourth aspect, the present invention pertains to a pharmaceutical blood coagulation factor replacement kit for use as disclosed herein, the kit comprising (i) a first composition comprising at least prothrombin (Factor II) and (ii) a second composition comprising Antithrombin III (ATIII), wherein said first composition and said second composition are provided within the kit in order to allow either (a) prior to administration for preparation of a mixture, having a molar ratio between ATIII to Factor II of at least 1:30 and/or (b) for co-administration of said mixture or compositions, provided that the molar ratio between administered ATIII to administered Factor II is of at least 1:30, wherein by administration of said compositions the patient's risk for a thromboembolic complication is reduced.

In a fifth aspect, the present invention relates to a pharmaceutical product comprising Antithrombin III (ATIII) for co-administration with a prothrombin (Factor II) comprising product
(i) for use in the treatment or prophylaxis of bleedings of patients having an acquired coagulation factor deficiency or
(ii) for use in the treatment or prophylaxis of bleedings of patients having a congenital deficiency of a coagulation factor;
wherein prothrombin (Factor II) and Antithrombin III (ATIII) are co-administered having a molar ratio between ATIII to Factor II of at least 1:30;
and wherein by co-administration of said product the patient's risk for a thromboembolic complication is reduced.

According to a further aspect, the present invention pertains to a pharmaceutical product comprising prothrombin (Factor II) for co-administration with an Antithrombin III (ATIII) comprising product (i) for use in the treatment or prophylaxis of bleedings of patients having an acquired coagulation factor deficiency or (ii) for use in the treatment or prophylaxis of bleedings of patients having a congenital deficiency of a coagulation factor;

wherein prothrombin (Factor II) and Antithrombin III (ATIII) are co-administered having a molar ratio between ATIII to Factor II of at least 1:30;

and wherein by co-administration of said product the patient's risk for a thromboembolic complication is reduced.

According to a further aspect, the present invention pertains to a blood coagulation factor replacement product for use according to any one of the preceding claims, wherein the product is a prothrombin complex concentrate (PCC) of either one of the following two types:

a 3-factor complex containing factors II, IX and X, or
a 4-factor complex additionally containing factor VII;

said product either comprises Antithrombin III (ATIII) with a molar ratio between ATIII to Factor II of below 1:30 or even comprises no ATIII;

the PCC is provided for co-administration with an ATIII comprising product (i) for use in the treatment or prophylaxis of bleedings of patients having an acquired coagulation factor deficiency or (ii) for use in the treatment or prophylaxis of bleedings of patients having a congenital deficiency of a coagulation factor;

wherein Factor II and ATIII are co-administered having a molar ratio between ATIII to Factor II of at least 1:30 when co-administered;

and wherein by co-administration of said PCC product together with ATIII the patient's risk for a thromboembolic complication is reduced.

In a further aspect, the present invention relates to a blood coagulation factor replacement product; said product comprising at least isolated prothrombin (Factor II) and isolated Antithrombin III (ATIII), wherein the molar ratio between ATIII to Factor II is at least 1:30. Said product has preferably a composition according to any one or more aspect(s) disclosed herein or to any one or more embodiments as disclosed herein.

According to a further aspect, the present invention pertains to the use of a blood coagulation factor replacement product as disclosed herein for the manufacture of a medicament for a treatment as disclosed herein.

According to a further aspect, the present invention pertains to a method of (i) treatment or prophylaxis of bleedings of patients having an acquired coagulation factor deficiency or (ii) treatment or prophylaxis of bleedings of patients having a congenital deficiency of a coagulation factor;

by administering a blood coagulation factor replacement product to said patient, said product comprising at least isolated prothrombin (Factor II) and isolated Antithrombin III (ATIII), wherein the molar ratio between ATIII to Factor II is at least 1:30;

and wherein by administration of said product the patient's risk for a thromboembolic complication is reduced.

The present invention therefore in addition relates in particular the following embodiments [1] to [48] or combinations thereof:

[1] A blood coagulation factor replacement product (i) for use in the treatment or prophylaxis of bleedings of patients having an acquired coagulation factor deficiency or (ii) for use in the treatment or prophylaxis of bleedings of patients having a congenital deficiency of a coagulation factor;

said product comprising at least isolated prothrombin (Factor II) and isolated Antithrombin III (ATIII), wherein the molar ratio between ATIII to Factor II is at least 1:30;

and wherein by administration of said product the patient's risk for a thromboembolic complication is reduced.

[2] The blood coagulation factor replacement product for use according to embodiment [1], wherein by administration of said product the patient's risk for a thromboembolic complication is reduced compared to a reference treatment, said reference treatment being identical to said treatment, except that the molar ratio between ATIII to Factor II of the product used in said reference treatment is below 1:30.

[3] The blood coagulation factor replacement product for use according to embodiment [1] or embodiment [2], wherein the product further comprises at least one of isolated coagulation factors selected from the group consisting of Factor IX, Factor X and Factor VII.

[4] The blood coagulation factor replacement product for use according to any one of the preceding embodiments, wherein the amount of blood loss of the patient following the treatment with the product is decreased compared to an amount of blood loss following a placebo treatment or without treatment, wherein the amount of blood loss is preferably reduced to an amount of below 75%, below 70%, below 60%, below 55%, below 50%, below 45%, below 40% or below 35% of the amount following placebo treatment or of the amount without treatment.

[5] The blood coagulation factor replacement product for use according to any one of the preceding embodiments, wherein the amount of blood loss of the patient following the treatment with the product is either essentially identical or only moderately increased when compared to a reference treatment, or wherein the amount of blood loss of the patient following the treatment with the product is decreased when compared to a reference treatment, preferably, the amount of blood loss of the patient following the treatment with the product being decreased when compared to a reference treatment by at least 5%, at least 10%, at least 15% or at least 20%, wherein said reference treatment is identical to said treatment, except that the molar ratio between ATIII to Factor II of the product used in said reference treatment is below 1:30.

[6] The blood coagulation factor replacement product for use according to any one of the preceding embodiments, wherein in case of the amount of blood loss of the patient following the treatment with the product is only moderately increased when compared to an amount of blood loss of a reference treatment, said moderate increase amounting to not more than 60%, not more than 50%, not more than 40%, not more than 30%, not more than 20%, not more than 15%, not more than 10% or not more than 5%, wherein said reference treatment is identical to said treatment, except that the molar ratio between ATIII to Factor II of the product used in said reference treatment is below 1:30.

[7] The blood coagulation factor replacement product for use according to any one of the preceding embodiments, wherein the value of time to hemostasis of the patient following the treatment with the product is decreased compared to the value of time to hemostasis following placebo treatment or without treatment, wherein said value of time to hemostasis following treatment with the product is preferably decreased by at least 25%, at least 30%, at least 35%, at least 40%, at least 45%, at least 50%, at least 55% or at least 60% compared of the value following placebo treatment or of the value without treatment.

[8] The blood coagulation factor replacement product for use according to any one of the preceding embodiments, wherein the value of time to hemostasis of the patient following the treatment with the product is either essentially identical or only moderately increased when compared to a reference treatment, or wherein the value of time to hemostasis of the patient following the treatment with the product is decreased when compared to a reference treatment, preferably, the value of time to hemostasis of the patient following the treatment with the product being decreased compared to a value following a reference treatment by at least 5%, by at least 10%, by at least 15% or by at least 20%, wherein said reference treatment is identical to said treatment, except that the molar ratio between ATIII to Factor II of the product used in said reference treatment is below 1:30.

[9] The blood coagulation factor replacement product for use according to any one of the preceding embodiments, wherein in case of the value of time to hemostasis of the patient following the treatment with the product is only moderately increased when compared to a reference treatment, said moderate increase of the value amounting to not more than 80%, not more than 70%, not more than 60%, not more than 50%, not more than 40%, not more than 30%, not more than 20% or not more than 10%, wherein said reference treatment is identical to said treatment, except that the molar ratio between ATIII to Factor II of the product used in said reference treatment is below 1:30.

[10] The blood coagulation factor replacement product for use according to any one of the preceding embodiments, wherein the value of prothrombin time (PT) and/or the value of activated partial thromboplastin time (aPTT) of the patient following the treatment with the product is decreased compared to the value of prothrombin time (PT) and/or the value of activated partial thromboplastin time (aPTT) of a reference treatment by a factor of at least 1.5, at least 2.0, at least 2.5, at least 3.0, at least 3.5, at least 4.0, at least 4.5, at least 5.0, at least 7, or at least 10 (in particular at about 1, at about 2, at about 3 and/or at about 4 hours following administration of the product), wherein said reference treatment is identical to said treatment, except that the molar ratio between ATIII to Factor II of the product used in said reference treatment is below 1:30.

[11] The blood coagulation factor replacement product for use according to any one of the preceding embodiments, wherein the value of prothrombin time (PT) and/or the value of activated partial thromboplastin time (aPTT) of the patient following the treatment with the product is essentially identical and/or has a maximum deviation of said value when compared to the respective value of prothrombin time (PT) and/or the respective value of activated partial thromboplastin time (aPTT) following placebo treatment or without treatment, provided that said maximum deviation does not exceed a factor of 5.0, of 4.0, of 3.0, of 2.5, of 2.0, or 1.5, in particular at about 1 hour, at about 2 hours, at about 3 hours and/or at about 4 hours following administration of the product.

[12] The blood coagulation factor replacement product for use according to any one of the preceding embodiments, wherein the value of thrombin generation, in particular of the Endogenous Thrombin Potential (ETP), of the patient following the treatment with the product is reduced when compared to a value of thrombin generation, in particular of the Endogenous Thrombin Potential (ETP), of a reference treatment by at least 5%, by at least 10%, by at least 15%, by at least 20%, by at least 25%, by at least 30%, by at least 35%, by at least 40%, by at least 45% or by at least 50%, in particular at 1 hour, at 2 hours and/or at 3 hours following administration of the product, wherein said reference treatment is identical to said treatment, except that the molar ratio between ATIII to Factor II of the product used in said reference treatment is below 1:30.

[13] The blood coagulation factor replacement product for use according to any one of the preceding embodiments, wherein the value of D-Dimer concentration (DD) of the patient's blood following the treatment with the product is reduced compared to the value of D-Dimer concentration (DD) of a reference treatment by a factor of at least 1.5, at least 2, at least 2.5, at least 3, at least 3.5, at least 4, at least 4.5, at least 5, at least 5.5, at least 6, at least 6.5, at least 7, at least 8, at least 9, or at least 10, in particular at about 1 hours, at about 2 hours, at about 3 hours and/or at about 4 hours following administration of the product, wherein said reference treatment is identical to said treatment, except that the molar ratio between ATIII to Factor II of the product used in said reference treatment is below 1:30.

[14] The blood coagulation factor replacement product for use according to any one of the preceding embodiments, wherein the product further comprises at least one of isolated coagulation inhibitors selected from the group consisting of Protein S, Protein C and Protein Z.

[15] The blood coagulation factor replacement product for use according to any one of the preceding embodiments, wherein the product further comprises heparin.

[16] The blood coagulation factor replacement product for use according to any one of the preceding embodiments, wherein the product further comprises albumin.

[17] The blood coagulation factor replacement product for use according to any one of the preceding embodiments, wherein the Factor II is non-activated and, if present in the coagulation factor replacement product, the coagulation factors Factor IX, Factor X and Factor VII are independently either non-activated or activated, preferably all of said Factors being non-activated.

[18] The blood coagulation factor replacement product for use according to any one of the preceding embodiments, wherein the product is administered to the patient either intravenously, topically or intraosseously. When provided intravenously, the product may be administered by intravenous infusion or by an intravenous bolus dose.

[19] The blood coagulation factor replacement product for use according to any one of the preceding embodiments, wherein the factor II is provided within the product with an activity level of between 10-80 IU/mL, between 15-60 IU/mL, preferably between 20-48 IU/mL.

[20] The blood coagulation factor replacement product for use according to any one of the preceding embodiments, wherein, if present in the coagulation factor replacement product, the coagulation factors Factor IX, Factor X, and Factor VII, are provided within the product independently with activity levels as follows:
Factor IX between 10-50 IU/mL, between 15-40 IU/mL, preferably 20-31 IU/mL,
Factor X between 10-100 IU/mL, between 15-80 IU/mL, preferably 22-60 IU/mL, and Factor VII between 5-50 IU/mL, between 5-40 IU/mL, preferably 10-25 IU/mL.

[21] The blood coagulation factor replacement product for use according to any one of the preceding embodiments, wherein, if present in the coagulation factor replacement product, the inhibitors Protein S, Protein C and Protein Z are provided within the product independently with activity levels as follows:
Protein S between 5-50 IU/mL, between 10-45 IU/mL, preferably 12-38 IU/mL,
Protein C between 10-60 IU/mL, between 10-50 IU/mL preferably 15-45 IU/mL, and
Protein Z between 5-60 IU/mL, between 5-50 IU/mL, preferably 10-45 IU/mL.

[22] The blood coagulation factor replacement product for use according to any one of the preceding embodiments, wherein the activity dosage of the administered replacement product is in a range between about 5 IU/kg to about 100 IU/kg, between about 10 IU/kg to about 75 IU/kg, or between about 10 IU/kg to about 50 IU/kg, provided that the activity is referring to the activity of factor II or, if present, of factor IX.

[23] The blood coagulation factor replacement product for use according to any one of embodiments [3] to [22], wherein the activity levels of the coagulation Factor II and Factor IX are in a balanced ratio, provided that the difference of the activity level of one of both factors over the other within the product does not exceed a factor of 3, 2.5, 2.0, 1.5, or 1.2.

[24] The blood coagulation factor replacement product for use according to any one of the preceding embodiments, wherein the molar ratio between ATIII to Factor II is not higher than 1:0.5.

[25] The blood coagulation factor replacement product for use according to any one of the preceding embodiments, wherein the molar ratio between ATIII to Factor II is within a range between 1:30 to 1:0.5, preferably within a range between 1:28 to 1:0.5, between 1:25 to 1:0.5, between 1:24 to 1:0.5, between 1:23 to 1:0.5, between 1:22 to 1:0.5, between 1:21 to 1:0.5, between 1:20 to 1:0.5, between 1:18 to 1:0.5, between 1:15 to 1:0.5, between 1:12 to 1:0.5, or between 1:10 to 1:0.5.

[26] The blood coagulation factor replacement product for use according to any one of the preceding embodiments, wherein the molar ratio between ATIII to Factor II is within a range between 1:30 to 1:1, preferably within a range between 1:28 to 1:1, between 1:25 to 1:1, between 1:24 to 1:1, between 1:23 to 1:1, between 1:22 to 1:1, between 1:21 to 1:1, between 1:20 to 1:1, between 1:18 to 1:1, between 1:15 to 1:1, between 1:12 to 1:1, or between 1:10 to 1:1.

[27] The blood coagulation factor replacement product for use according to any one of the preceding embodiments, wherein the molar ratio between ATIII to Factor II is within a range between 1:30 to 1:2, preferably within a range between 1:28 to 1:2, between 1:25 to 1:2, between 1:24 to 1:2, between 1:23 to 1:2, between 1:22 to 1:2, between 1:21 to 1:2, between 1:20 to 1:2, between 1:18 to 1:2, between 1:15 to 1:2, between 1:12 to 1:2, or between 1:10 to 1:2.

[28] The blood coagulation factor replacement product for use according to any one of the preceding embodiments, wherein the ATIII is a plasma derived protein or a recombinant protein.

[29] The blood coagulation factor replacement product for use according to any one of the preceding embodiments, wherein the factor II and/or, if present, at least one of further coagulation factors selected from the group consisting of Factor IX, Factor X and Factor VII are either recombinant proteins or plasma derived proteins.

[30] The blood coagulation factor replacement product for use according to any one of the preceding embodiments, wherein tranexamic acid (TXA) is co-administered, preferably at an amount in a range between 10 to 20 mg/kg bodyweight.

[31] The blood coagulation factor replacement product for use according to any one of the preceding embodiments, wherein said treatment or prophylaxis comprises treatment and perioperative prophylaxis of bleedings in acquired deficiency of the prothrombin complex coagulation factors, in particular a deficiency caused by treatment with vitamin K antagonists, or in case of overdose of vitamin K antagonists, when rapid correction of the deficiency is required; or wherein said treatment or prophylaxis comprises treatment and perioperative prophylaxis of bleedings in congenital deficiency of any vitamin K dependent coagulation factor, in particular, when purified specific coagulation factor products are not available.

[32] The blood coagulation factor replacement product for use according to any one of the preceding embodiments, wherein the patient suffers from any kind of trauma-associated coagulopathy including perioperative bleeding associated coagulopathy.

[33] The blood coagulation factor replacement product for use according to any one of the preceding embodiments, wherein the patient suffers from severe bleeding and has a deficiency of vitamin K-dependent coagulation factors, in particular has an acquired coagulation disturbance, e.g. a liver disease or the like, or has hemophilia B, in particular with inhibitors.

[34] The blood coagulation factor replacement product for use according to any one of the preceding embodiments, wherein the patient has previously been treated with a vitamin K antagonist, in particular an oral vitamin K antagonist, or with a directly acting oral anticoagulant (DOAC/NOAC), preferably a direct FIIa or FXa inhibitor, and is in need for a rapid reversal of the anticoagulant effect of the vitamin K antagonist or of the DOAC/NOAC.

[35] The blood coagulation factor replacement product for use according to any one of the preceding embodiments, wherein the patient before treatment with said product has at least one of the following conditions of coagulopathy compared to a healthy subject:
more than 1.5 fold prolongation of prothrombin time (PT),
more than 1.5 fold prolongation of activated partial thromboplastin time (aPTT),
more than 1.5 fold prolongation of whole blood clotting time (WBCT),
the rotational thromboelastography parameters EXTEM-CT or EXTEM-CFT, together with a reduction in FIBTEM-MCF, or
loss or substantial reduction of the coagulation factors of the prothrombin complex.

[36] The blood coagulation factor replacement product for use according to any one of the preceding embodiments, wherein in addition to the treatment with said product the patient is in advance, simultaneously or subsequently treated with at least one of the following options:
administration of volume expanders or resuscitation fluids, in particular administration of Ringer's lactate, saline and/or hydroxyethyl starch (HES/HAES),
administration of packed red blood cells (PRBC), administration of fresh frozen plasma (FFP),
administration of platelets, or
administration of fresh whole blood.

[37] The blood coagulation factor replacement product for use according to any one of the preceding embodiments, wherein in addition to the treatment with said product the patient is in advance, simultaneously or subsequently treated with a replacement product, such as cryoprecipitate, or with a fibrinogen concentrate, preferably the replacement product or the fibrinogen concentrate being administered at a fibrinogen amount in a range between 5 mg/kg and 150 mg/kg bodyweight, between 10 mg/kg and 100 mg/kg, between 20 mg/kg and 80 mg/kg and preferably between 25 mg/kg and 60 mg/kg bodyweight.

[38] The blood coagulation factor replacement product for use according to any one of the preceding embodiments, wherein the product is used as first-line monosubstance treatment, preferably in the treatment of significant bleeding, in particular perioperative or following trauma, preferably associated with deficiency of vitamin K-dependent coagulation factors, further preferred outside Vitamin K anticoagulation.

[39] The blood coagulation factor replacement product for use according to any one of the preceding embodiments, wherein the patient before treatment has an injury severity score (ISS)>16 and/or severe shock.

[40] The blood coagulation factor replacement product for use according to any one of embodiments [3] to [39], wherein the product is a prothrombin complex concentrate (PCC) of either one of the following two types:
a 3-factor complex comprising factors II, IX and X; or
a 4-factor complex additionally comprising factor VII;
said product additionally comprises Antithrombin III (ATIII), wherein the molar ratio between ATIII to Factor II is at least 1:30. In general, a prothrombin complex concentrate (PCC) according to present invention is also referred to as a modified PCC herein in order to emphasize the elevated ATIII content compared to a PCC as known in the prior art.

[41] The blood coagulation factor replacement product for use according to any one of the preceding embodiments, wherein the reduced risk for a thromboembolic complication is manifested by a reduction of arterial or venous thrombosis, myocardial infarction, and/or disseminated intravascular coagulation (DIC).

[42] A combination of a prothrombin complex concentrate (PCC) and Antithrombin III (ATIII)
(i) for use in the treatment or prophylaxis of bleedings of patients having an acquired coagulation factor deficiency or
(ii) for use in the treatment or prophylaxis of bleedings of patients having a congenital deficiency of a coagulation factor,
the PCC comprising at least prothrombin (Factor II), Factor IX, Factor X and optionally Factor VII, provided that the molar ratio between administered ATIII to Factor II is at least 1:30; and
wherein by administration of said combination the patient's risk for a thromboembolic complication is reduced.

[43] A combination therapy comprising administration of a prothrombin complex concentrate (PCC) and co-administration of Antithrombin III (ATIII)
(i) for treatment or prophylaxis of bleedings of patients having an acquired coagulation factor deficiency or
(ii) for treatment or prophylaxis of bleedings of patients having a congenital deficiency of a coagulation factor,
the PCC comprising at least prothrombin (Factor II), Factor IX, Factor X and optionally Factor VII, provided that the molar ratio between administered ATIII to administered Factor II is at least 1:30; and
wherein by administration of said combination the patient's risk for a thromboembolic complication is reduced.

[44] A pharmaceutical blood coagulation factor replacement kit for use according to any one of embodiments [1] to [41], the kit comprising (i) a first composition comprising at least prothrombin (Factor II) and (ii) a second composition comprising Antithrombin III (ATIII), wherein said first composition and said second composition are provided within the kit in order to allow either (a) prior to administration for preparation of a mixture, having a molar ratio between ATIII to Factor II of at least 1:30 and/or (b) for co-administration of said mixture or compositions, provided that the molar ratio between administered ATIII to administered Factor II is at least 1:30, wherein by administration of said compositions the patient's risk for a thromboembolic complication is reduced.

[45] A pharmaceutical product comprising Antithrombin III (ATIII) for co-administration with a prothrombin (Factor II) comprising product
(i) for use in the treatment or prophylaxis of bleedings of patients having an acquired coagulation factor deficiency or
(ii) for use in the treatment or prophylaxis of bleedings of patients having a congenital deficiency of a coagulation factor;
wherein prothrombin (Factor II) and Antithrombin III (ATIII) are co-administered having a molar ratio between ATIII to Factor II of at least 1:30;
and wherein by co-administration of said products the patient's risk for a thromboembolic complication is reduced.

[46] A pharmaceutical product comprising prothrombin (Factor II) for co-administration with an Antithrombin III (ATIII) comprising product
(i) for use in the treatment or prophylaxis of bleedings of patients having an acquired coagulation factor deficiency or
(ii) for use in the treatment or prophylaxis of bleedings of patients having a congenital deficiency of a coagulation factor;
wherein prothrombin (Factor II) and Antithrombin III (ATIII) are co-administered having a molar ratio between ATIII to Factor II of at least 1:30;
and wherein by co-administration of said products the patient's risk for a thromboembolic complication is reduced.

[47] A blood coagulation factor replacement product for use according to any one of the embodiments [1]-[41], wherein the product is a prothrombin complex concentrate (PCC) of either one of the following two types:
a 3-factor complex containing factors II, IX and X, or
a 4-factor complex additionally containing factor VII;
said product either comprises Antithrombin III (ATIII) with a molar ratio between ATIII to Factor II of below 1:30 or even comprises no ATIII;
the PCC is provided for co-administration with an ATIII comprising product
(i) for use in the treatment or prophylaxis of bleedings of patients having an acquired coagulation factor deficiency or (ii) for use in the treatment or prophylaxis of bleedings of patients having a congenital deficiency of a coagulation factor;

wherein Factor II and ATIII are co-administered having a molar ratio between ATIII to Factor II of at least 1:30 when co-administered;

and wherein by co-administration of said PCC product together with ATIII the patient's risk for a thromboembolic complication is reduced.

[48] A method of
(i) treatment or prophylaxis of bleedings of patients having an acquired coagulation factor deficiency or
(ii) treatment or prophylaxis of bleedings of patients having a congenital deficiency of a coagulation factor;

by administering a blood coagulation factor replacement product to said patient, said product comprising at least isolated prothrombin (Factor II) and isolated Antithrombin III (ATIII), wherein the molar ratio between ATIII to Factor II is at least 1:30;

and wherein by administration of said product the patient's risk for a thromboembolic complication is reduced.

The embodiments [1] to [48] can be combined with any one or more of the features of other embodiments or aspects disclosed herein.

DEFINITIONS

Figure 1:
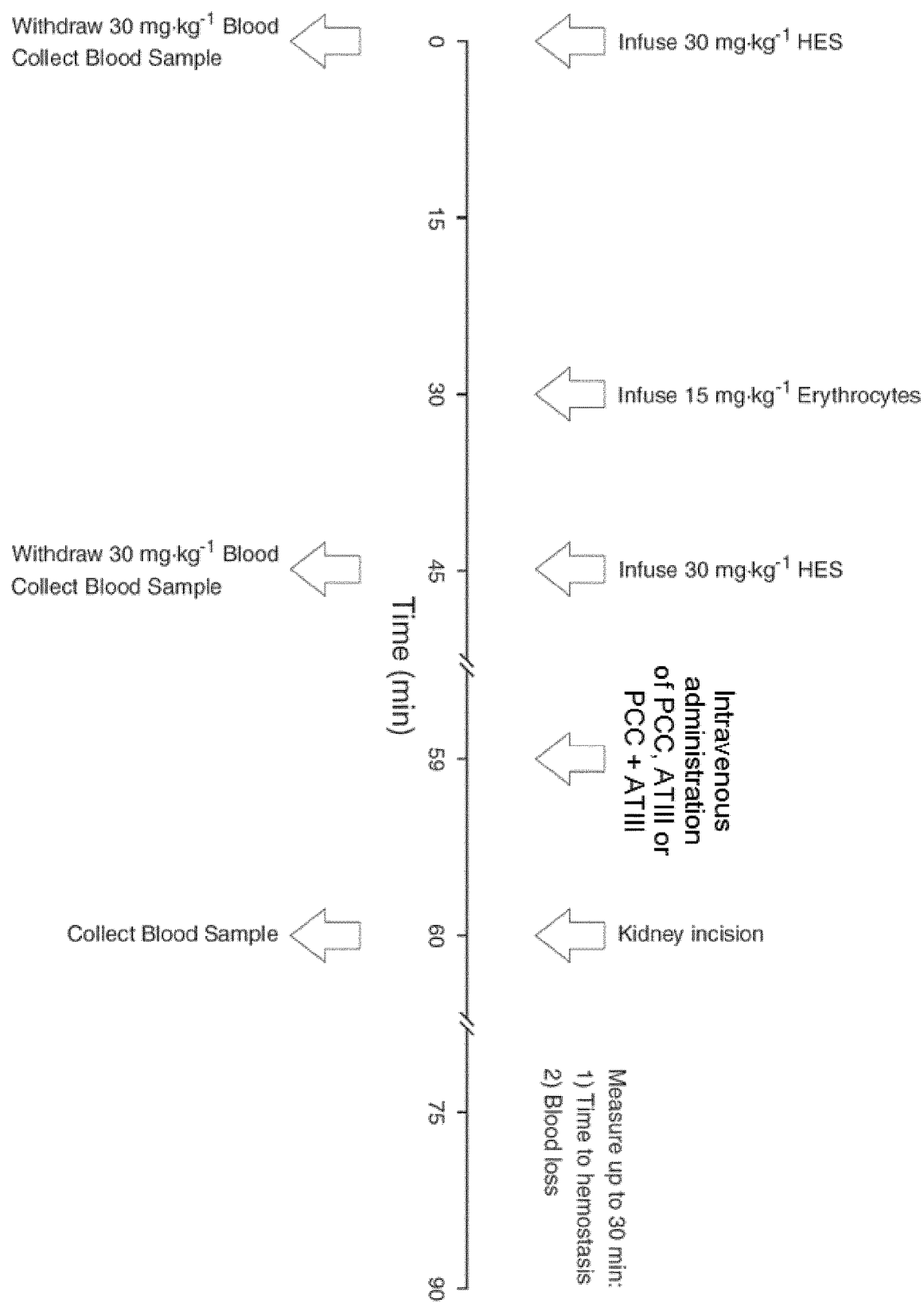
FIG. 1 shows the study procedures for hemodilution, treatment, experimental kidney trauma and assessment of hemostatic effect. Abbreviations: HES, hydroxyethyl starch; PCC (prothrombin complex concentrate), ATIII (antithrombin III)

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight, length, or other unit described herein.

An "Antithrombin III (ATIII)" according to the present invention is a functional plasma proteinase inhibitor ATIII, in particular an isolated, i.e. purified, functional ATIII. ATIII is preferably human ATIII.

A "coagulation factor" according to the present invention is a functional coagulation factor, in particular an isolated, i.e. purified, functional coagulation factor. The coagulation factor is preferably a human coagulation factor.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

"Isolated" in the sense of this inventions means, that the respective coagulation factor or mixture of coagulation factors or ATIII have been purified from either human plasma (plasma derived) or, if produced recombinantly, from the culture medium. Purified in the sense of this invention means any type of purification which leads to a higher biological activity of said coagulation factor or mixture of coagulation factors or ATIII per mg of total protein content or to a higher biological activity of said coagulation factor or mixture of coagulation factors or ATIII per ml of liquid which is finally administered to the patient, as compared to the solution from which the respective coagulation factor or mixture of coagulation factors or ATIII was obtained originally.

One International Unit ("IU") of activity of a coagulation factor or ATIII is equivalent to that quantity of the respective coagulation factor or of ATIII in one mL of normal human plasma.

A blood coagulation factor replacement product of the invention may be provided and referred to as a modified prothrombin complex concentrate (PCC). A modified Prothrombin complex concentrate (PCC) in the meaning of the present invention comprises a combination of at least isolated coagulation factors FII, FIX, FX (also herein referred to as 3-factor complex) or of isolated coagulation factors FII, FIX, FX and FVII (also herein referred to as 4-factor complex). A modified PCC according to the invention—in contrast to a PCC as known from the prior art, i.e. a conventional PCC—additionally comprises at least Antithrombin III (ATIII), wherein the molar ratio between ATIII to Factor II is at least 1:30. The isolated coagulation factors FII, FIX, FX and FVII of a modified PCC may be derived from human blood or such a PCC can be reconstituted from recombinantly expressed coagulation factors, wherein the ratios of antigen and activity of said recombinantly expressed coagulation factors FVII, FIX, FX and FVII correspond to PCCs derived from blood, provided that the modified PCC additionally comprises at least Antithrombin III (ATIII), wherein the molar ratio between ATIII to Factor II is at least 1:30.

A blood coagulation factor replacement product of the invention encompasses each individual coagulation factor present in a liquid or if stored lyophilized in the liquid after reconstitution prior to injection. If not indicated otherwise, the concentrations of coagulation factors provided with a product of the invention, in particular in IU/mL, refer to the concentration of a coagulation factor present in a liquid or if the product is stored lyophilized in the liquid after reconstitution prior to injection.

A "patient" or "subject" to whom a product of the invention is administered is either an animal or a human, preferably a human. In certain aspects, the human is a pediatric patient. In other aspects, the human is an adult patient.

"Substantially" or "essentially" means nearly totally or completely, for instance, 95%, 96%, 97%, 98%, 99% or greater of some given quantity.

DETAILED DESCRIPTION OF THE INVENTION

Coagulation Factors

A functional coagulation factor II (FII) displays the biological activity of prothrombin, which represents the inactive proenzyme of thrombin (FIIa). After activation of the coagulation cascade the conversion of prothrombin to thrombin takes place, the latter multiple activating functions in the coagulation system include among others the conversion of fibrinogen to fibrin, activation of coagulation factor XIII (FXIII) to activated coagulation factor XIII (XIIIa), activation of FV and FVIII to FVa and VIIIa, platelet activation after partial proteolysis of the thrombin receptor.

A functional coagulation factor IX (FIX) displays the biological activity of inactive FIX, which is converted upon coagulation activation to the active FIXa. FIXa forms a complex with its coenzyme FVIIIa and represents the tenase complex, which cleaves the inactive FX to its active form FXa.

A functional coagulation factor X (FX) displays the biological activity of inactive FX which is converted to active FXa after coagulation activation. FXa forms a complex with its coenzyme FVa which represents the prothrombinase complex which cleaves the inactive prothrombin (FII) into the active thrombin (Ala).

A functional coagulation factor FVII (FVII) displays the biological activity of inactive FVII which is converted during the activation of coagulation to FVIIa. FVIIa together with tissue factor converts the inactive FX to the active FXa. Additionally FVIIa can convert inactive FIX to active FIXa.

The activity of the coagulation factors discussed above can be measured according to L. Thomas: Clinical Laboratory Diagnostics, TH-Books, Frankfurt, 1998, Chapter 17.

The coagulation factors used herein can be obtained from human plasma or serum or can be obtained recombinantly.

Coagulation factors as used in the present invention comprise proteins that have the amino acid sequence of native human coagulation factors. Also comprised are coagulation factors with a slightly modified amino acid sequence, for instance, a modified N-terminal end including N-terminal amino acid deletions or additions so long as those proteins substantially retain the activity of the coagulation factors. The coagulation factors within the above definition also comprise natural allelic variations that may exist and occur from one individual to another. The coagulation factors within the above definition further comprise variants of such coagulation factors. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, e.g. addition of a methionine residue at the N-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, (6) aromatic amino acids. Examples of such conservative substitutions are shown in the following table.

| (1) | Alanine | Glycine | | |
| (2) | Aspartic acid | Glutamic acid | | |
| (3a) | Asparagine | Glutamine | | |
| (3b) | Serine | Threonine | | |
| (4) | Arginine | Histidine | Lysine | |
| (5) | Isoleucine | Leucine | Methionine | Valine |
| (6) | Phenylalanine | Tyrosine | Tryptophane | |

Functional coagulation factors as used in this invention comprise coagulation factor molecules displaying biological activity either in solution and/or on cellular surfaces as described above.

The term "recombinant" means, for example, that the coagulation factor or coagulation factor variant has been produced in a host organism by genetic engineering techniques.

The host cells of the invention may be employed in a method of producing human coagulation factors. The method comprises:

a) culturing host cells of the invention under conditions such that one or more human coagulation factors is/are expressed; and b) optionally recovering one or more human coagulation factors from the host cells or from the culture medium.

Degree and location of glycosylation or other post-translation modifications may vary depending on the chosen host cells and the nature of the host cellular environment. When referring to specific amino acid sequences, posttranslational modifications of such sequences are encompassed in this application.

The production of recombinant proteins at high levels in suitable host cells, requires the assembly of the above-mentioned modified cDNAs into efficient transcriptional units together with suitable regulatory elements in a recombinant expression vector, that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the coagulation factors. Preferably this cell line should be an animal cell-line of vertebrate origin in order to ensure correct folding, Gla-domain synthesis, disulfide bond formation, asparagine-linked glycosylation, O-linked glycosylation, and other post-translational modifications as well as secretion into the cultivation medium. Examples of other post-translational modifications are hydroxylation and proteolytic processing of the nascent polypeptide chain. Examples of cell lines that can be used are monkey COS-cells, mouse L-cells, mouse C127-cells, hamster BHK-21 cells, human embryonic kidney 293 cells, and preferentially hamster CHO-cells. Due to its complex post-translational modifications recombinant coagulation factors are preferably expressed in human cell lines.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNAs can also be introduced into animal cells together with another recombinant gene, which may function as a dominant selectable marker in these cells in order to facilitate the isolation of specific cell clones, which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated into the genome of the host cell, frequently resulting in a tight physical linkage between the different transcription units.

Other types of selectable marker genes, which can be used together with the cDNA of the desired protein, are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the coagulation factor cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant proteins The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody, which is immobilised on a solid support. After desorption, the protein can be further purified by a variety of chromatographic techniques based on the above properties.

It is preferred to purify the coagulation factors of the present invention, irrelevant whether produced by recombinant means or obtained from human plasma, to ≥60% purity, more preferably ≥80% purity, and particularly preferred is a pharmaceutically pure state that is greater than 95% pure with respect to contaminating macromolecules, particularly other proteins and nucleic acids, and free of infectious and pyrogenic agents.

The coagulation factors as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially the compositions of the invention are administered systemically. For systemic use, the coagulation factors of the invention are formulated for parenteral (e.g. intravenous, subcutaneous, intramuscular, intraperitoneal, intracerebral, intrapulmonar, intranasal or transdermal or vaginal) or enteral (e.g., oral, or rectal) delivery according to conventional methods. The most preferential routes of administration are intravenous and subcutaneous administration. The formulations can be administered continuously by infusion or by bolus injection. Some formulations encompass slow release systems.

The coagulation factors of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

Antithrombin III (ATIII)

Functional Antithrombin III (ATIII) displays the biological activity of the plasma proteinase inhibitor Antithrombin III. Human ATIII is a glycoprotein having a molecular weight of about 58 kDa with 432 amino acids. The plasma proteinase inhibitor ATIII inactivates thrombin and enzymes responsible for generation of thrombin. ATIII exhibits sequence, structural as well as functional homology to members of the serpin gene family. Serpins inhibit their target enzymes via a suicide-substrate inhibition mechanism. ATIII in particular inhibits thrombin, activated Factor X (FXa) and activated Factor IX (FIXa).

Antithrombin III (ATIII) as used in the present invention comprises preferably proteins that have the amino acid sequence of native human ATIII. Also comprised is ATIII with a slightly modified amino acid sequence, for instance, a modified N-terminal end including N-terminal amino acid deletions or additions so long as those proteins substantially retain the activity of ATIII. The ATIII within the above definition also comprise natural allelic variations that may exist and occur from one individual to another. The ATIII within the above definition further comprise variants of such ATIII. Such variants differ in one or more amino acid residues from the wild type sequence. Examples of such differences are provided supra for coagulation factors. Functional ATIII as used in this invention comprise ATIII molecules displaying biological activity either in solution and/or on cellular surfaces as described above. The term "recombinant" means, for example, that the ATIII or ATIII variant has been produced in a host organism by genetic engineering techniques as already described supra.

Molar Ratios

According to the present invention, prothrombin (Factor II) and Antithrombin III (ATIII) are used in treatment of a patient in need thereof in a molar ratio between administered ATIII to administered Factor II of at least about 1:30. Hence, the molar ratio between ATIII to Factor II according to the invention being at least about 1:30 is particularly understood herein as a lower limit of ATIII.

A product of the invention comprises at least prothrombin (Factor II) and Antithrombin III (ATIII), wherein the molar ratio between ATIII to Factor II is at least 1:30. Without wishing to be bound by any theory it is believed that said minimal molar ATIII level in relation to prothrombin ensures in particular that upon activation of prothrombin, sufficient ATIII molecules are available to bind excess thrombin or Factor Xa, limiting excess thrombin generation and/or fibrin formation, and therefore minimizing or inhibiting the risk of thromboembolic events, i.e. thromboembolic complications. Therefore, said ATIII levels ensure consequently improved safety of the treatment or of the product. The molar ratio between ATIII to Factor II is according to a further preferred embodiment at least 1:29, at least 1:28, at least 1:27, at least 1:26, at least 1:25, at least 1:24, at least 1:23, at least 1:22, at least 1:21, at least 1:20, at least 1:19, at least 1:18, at least 1:17, at least 1:16 at least 1:15, at least 1:14, at least 1:13, at least 1:12, at least 1:11, or even at least 1:10.

The molar ratio between ATIII to Factor II is according to a preferred embodiment not higher than about 1:0.5. Without wishing to be bound by any theory it is believed that this molar upper limit of ATIII level in relation to prothrombin ensures in particular that upon activation of prothrombin, sufficient free thrombin remains available to catalyze the reaction of fibrinogen to fibrin. Therefore, said ATIII levels ensure adequate thrombin generation, fibrin formation and consequently provide adequate efficacy. The molar ratio between ATIII to Factor II is according to a further preferred embodiment not higher than about 1:1. The molar ratio between ATIII to Factor II is according to a further preferred embodiment not higher than about 1:2.

Any of said lower limit of ATIII can be combined with any of said upper limit of ATIII.

The molar ratio between ATIII to Factor II is further preferred within a range between 1:30 to 1:0.5, preferably within a range between 1:10 to 1:0.5. The molar ratio between ATIII to Factor II is further preferred within a range between 1:30 to 1:1, preferably between 1:10 to 1:1. According to a further preferred embodiment, the molar ratio between ATIII to Factor II is within a range between 1:10 to 1:2.

Any molar ratios according to the invention refer to a ratio of the molar concentration of the respective proteins.

Molar ratios in terms of present invention are formed over the molar concentration of the proteins to be administered before administration, in particular within a blood coagulation factor replacement product. Since the patient under circumstances already has a certain endogenous level of one or more of the proteins to be administered, the molar ratio resulting in vivo may differ from the molar ratio of the proteins according to the invention.

The molar ratio between ATIII to Factor II is further preferred within a range between 1:30 to 1:0.5, preferably within a range between 1:28 to 1:0.5, between 1:25 to 1:0.5, between 1:24 to 1:0.5, between 1:23 to 1:0.5, between 1:22 to 1:0.5, between 1:21 to 1:0.5, between 1:20 to 1:0.5, between 1:18 to 1:0.5, between 1:15 to 1:0.5, between 1:12 to 1:0.5, or between 1:10 to 1:0.5.

The molar ratio between ATIII to Factor II is further preferred within a range between 1:30 to 1:1, preferably within a range between 1:28 to 1:1, between 1:25 to 1:1, between 1:24 to 1:1, between 1:23 to 1:1, between 1:22 to 1:1, between 1:21 to 1:1, between 1:20 to 1:1, between 1:18 to 1:1, between 1:15 to 1:1, between 1:12 to 1:1, or between 1:10 to 1:1.

The molar ratio between ATIII to Factor II is further preferred within a range between 1:30 to 1:2, preferably within a range between 1:28 to 1:2, between 1:25 to 1:2, between 1:24 to 1:2, between 1:23 to 1:2, between 1:22 to 1:2, between 1:21 to 1:2, between 1:20 to 1:2, between 1:18 to 1:2, between 1:15 to 1:2, between 1:12 to 1:2, or between 1:10 to 1:2.

Further details of the treatment in accordance with the invention are described further below.

The molar ratio of ATIII to FII is calculated herein preferably based on the following assumptions:
Molecular weight of ATIII=58,000 Da
Molecular weight of FII=72,000 Da
Plasma concentration of ATIII=2.4 µmol/L (healthy subject)
Plasma concentration of FII=1.4 µmol/L (healthy subject)
1 IU/kg ATIII=140 µg/kg=2.4 nmoles/kg ATIII
1 IU/kg FII=90 µg/kg FII=1.25 nmoles/kg FII
1 IU ATIII:1 IU FII is equal to 1.92 moles ATIII:1 mole FII, hence is approx. equal to 2 moles ATIII:1 mole FII.

Heparin

A "Heparin" according to the present invention is a functional Heparin, in particular an isolated, i.e. purified, functional Heparin. Functional Heparin displays the biological activity of a cofactor for ATIII. Heparin and HSPGs (heparin sulfate proteoglycans) serve as pharmaceutical and physiologic cofactors for ATIII, respectively. A functional Heparin of the invention comprises a specific pentasaccharide sequence as well known in the art suitable for activation of ATIII. Inhibition rates of ATIII for thrombin, activated Factor X (FXa) and activated Factor IX (FIXa) are accelerated by Heparin.

Functional Heparin can be selected from the group consisting of unfractionated heparin (UFH), Low-molecular-weight heparin (LMWH) and synthetic pentasaccharide factor Xa inhibitor or a mixture of them. UFH is the preferred type of Heparin for the herein described use. For the heparin mediated activation of ATIII for inhibition of FXa said specific pentasaccharide sequence suffices. However, for accelerated thrombin inhibition by ATIII at least 18 saccharide units of heparin are required. UFH is the preferred type of Heparin for the herein described use, in particular, when amplification of the ATIII thrombin inhibition by heparin is intended.

A blood coagulation factor replacement product according to the invention may comprise heparin, wherein the heparin is preferably provided within the product with activity level of between 0.1-10 IU/mL, between 0.2-5.0 IU/mL, between 0.2-3.0 IU/mL, and preferably between 0.4-2.0 IU/mL.

Albumin

A blood coagulation factor replacement product according to the invention, may further comprise albumin.

Albumin according to the present invention is in particular an isolated, i.e. purified, albumin protein. The albumin is preferably a human albumin. The albumin is preferably a plasma derived protein.

Blood Loss

Blood loss as used herein is the total volume of blood derived from tissue injury as collected during the observation period.

Thrombus Score

Thrombus score as used herein describes the size and extent of the thrombus/thrombi derived from the dissected vein segment following 30 min of venous stasis. The thrombus score is used as a surrogate marker for the risk of thromboembolic events.

Score 0—no thrombus

Score 1—one or several small thrombi with wet weight not measurable

Score 2—one or several thrombi with measurable wet weight

Score 3—fully occluding thrombus

Thrombus Wet Weight

Thrombus wet weight describes the wet weight of the thrombus derived from the dissected vein segment following 30 min of venous stasis and further characterizes the thrombi detected.

D-Dimer

D-dimer (or D dimer) is a fibrin degradation product (or FDP), a small protein fragment present in the blood after a blood clot is degraded by fibrinolysis. D-dimers are not normally present in human blood plasma, except when the coagulation system has been activated, for instance because of the presence of thrombosis or disseminated intravascular coagulation (DIC).

Time to Hemostasis

Time to hemostasis describes the time from placing the tissue injury to full cessation of bleeding within the observation period applied and is used as a direct indicator of hemostatic efficacy of the intervention tested.

Acquired Coagulation Factor Deficiency

An acquired coagulation factor deficiency in accordance with present invention is in particular an acquired prothrombin complex factor deficiency, preferably caused by vitamin K deficiency or by overdose of oral anticoagulants. Impaired synthesis of prothrombin complex factors can be the result of a liver dysfunction or liver transplantation. Treatment as described herein is in particular of advantage when the patient is bleeding or a surgery is intended. In all these situations the administration of a blood coagulation factor replacement product of the invention may be useful. Patients taking oral anticoagulants show an increased predisposition to thromboembolisms, thus treatment with a blood coagulation factor replacement product of present invention is of particular advantage because of the herein described reduction of patient's risk for a thromboembolic complication. Oral anticoagulants in term of present invention particularly comprise oral vitamin K antagonists or directly acting oral anticoagulants (DOACs/NOACs).

An acquired coagulation factor deficiency in accordance with present invention can according to a further aspect be the result of a disseminated intravascular coagulopathy (DIC), also known as consumptive coagulopathy. A DIC is a pathological process characterized by the widespread activation of the clotting cascade that results in the formation of blood clots in small blood vessels throughout the body and generation and deposition of fibrin. This may lead to microvascular thrombi in various organs and contributing to multiple organ dysfunction syndrome and multiple organ failure. In addition, as the coagulation process consumes coagulation factors and platelets, normal clotting is impaired and diffuse bleeding can occur from various sites. Derangement of the fibrinolytic system further contributes to intravascular clot formation, but in some cases, accelerated fibrinolysis may also lead to severe bleeding. The subcommittee on DIC of the International Society on Thrombosis and Haemostasis has suggested the following definition for DIC: "An acquired syndrome characterized by the intravascular activation of coagulation with loss of localization arising from different causes. It can originate from and cause damage to the microvasculature, which if sufficiently severe, can produce organ dysfunction."

DIC does not occur by itself but only as a complicating factor from another underlying condition, usually in those with a critical illness. The combination of widespread loss of tissue blood flow and simultaneous bleeding leads to an increased risk of death in addition to that posed by the underlying disease. However, current coagulation factor concentrates as known in the prior art are not recommended for this clinical situation. According to another aspect, the patient's risk of occurrence of a DIC or the risk of occurrence of DIC like symptoms upon administration of a conventional blood coagulation factor replacement product as known in the art—which has been observed at least if administered at high dosages—may be reduced by application of a blood coagulation factor replacement product according to the invention, i.e. having a molar ratio between ATIII to Factor II is at least 1:30.

Congenital Deficiency of a Coagulation Factor

A congenital deficiency of a coagulation factor in terms of present invention can be any patient's prothrombin complex factor deficiency, in particular congenital prothrombin deficiency or congenital factor X deficiency. In addition, a congenital deficiency of a coagulation factor in terms of present invention can be any patient's prothrombin complex factor deficiency in clinical situations where other therapeutic measures are not indicated or do not lead to the expected therapeutic effect. One not limiting example may be the emergency situation, when specific clotting factor or inhibitor concentrates are not available. Examples of the congenital deficiencies are hemophilia B, congenital factor VII deficiency or congenital protein C deficiency. The stop or prevention of bleedings in such patients may be required under said circumstances.

The bleeding in terms of present invention can be a manifest bleeding or a bleeding occurring perioperatively or after a traumatic event. In all these situations the administration of a blood coagulation factor replacement product of the invention may be indicated.

Thromboembolic Complication

Thromboembolism encompasses two interrelated conditions that are part of the same spectrum, deep venous thrombosis (DVT) and pulmonary embolism (PE). The spectrum of disease ranges from clinically unsuspected to clinically unimportant to massive embolism causing death. According the Virchow trias three factors are important in the development of thrombosis: (1) impairment of blood flow (stasis), (2) vascular injury, and (3) alterations of the blood (hypercoagulability). Alterations of the blood can also be drug induced. The blood coagulation factor replacement product of present invention could be used for treatment of any one of said conditions. By administration of the product of the invention the patient's risk for a thromboembolic complication is reduced.

Trauma/Polytrauma

A trauma in terms of present invention is preferably characterized by an injury to several (>1) physical regions or organ systems, in particular where at least one injury or the combination of several injuries is life threatening, in particular with the severity of injury being >16 on the scale of the Injury Severity Score (ISS). The polytrauma by definition should be differentiated from multiple injuries, which are not life threatening. The blood coagulation factor replacement product of present invention could be preferably used for treatment of any one of said conditions.

Trauma-Induced Coagulopathy

Hemorrhagic shock from blood loss is a critical cause of mortality in severely injured patients. The underlying pathophysiology of life-threatening bleeding is usually caused by a combination of traumatic injury and coagulopathy. The causes of coagulopathy are multifactorial and interrelated; these include consumption and dilution of coagulation factors and platelets, dysfunction of platelets and the coagulation system, increased fibrinolysis, disturbance of the coagulation system by the infusion of solutions (crystalloids and colloids), and hypocalcaemia.

Besides an acute intrinsic coagulopathy arising in severely injured trauma patients is termed trauma-induced coagulopathy (TIC) and is an emergent property of tissue injury combined with hypoperfusion contributing to blood loss. Mechanisms contributing to TIC include anticoagulation, consumption, platelet dysfunction, and hyperfibrinolysis. The blood coagulation factor replacement product of present invention could be used preferably for treatment of any one of said conditions.

Major/Manifest Bleeding

Any kind of bleeding can be a condition for which the product of the invention could be suitable treatment. Hemorrhaging is stratified into four classes by the American College of Surgeons' advanced trauma life support (ATLS) (Manning, J E "Fluid and Blood Resuscitation" in Emergency Medicine: A Comprehensive Study Guide. J E Tintinalli Ed. McGraw-Hill: New York 2004. p 227). Bleeding arises due to either traumatic injury, underlying medical condition, or a combination. The blood coagulation factor replacement product of present invention could be used preferably for treatment of any one of said conditions. The terms major, manifest, severe and significant for characterization of bleeding or hemorrhaging are used synonymously herein.

Hence, the blood coagulation factor replacement product of the invention may preferably be used in the treatment or prophylaxis of bleedings of patients having an acquired coagulation factor deficiency and/or in the treatment or prophylaxis of bleedings of patients having a congenital deficiency of a coagulation factor.

More specifically, the blood coagulation factor replacement product of the invention may preferably be used in the treatment or prophylaxis of one or more of the conditions selected from the group consisting of trauma; polytrauma; trauma-induced coagulopathy; major or manifest or severe or significant bleeding; any kind of trauma-associated coagulopathy; perioperative bleeding associated coagulopathy; deficiency of vitamin K-dependent coagulation factors; acquired coagulation disturbance, e.g. a liver disease or the like; hemophilia B; hemophilia B with inhibitors; a patient previously been treated with an oral vitamin K antagonist or with a directly acting oral anticoagulant (DOAC/NOAC) and being in need for a rapid reversal of the anticoagulant effect of the vitamin K antagonist or of the DOAC/NOAC; significant bleeding, e.g. perioperative, following trauma and the like, associated with deficiency of vitamin K-dependent coagulation factors, particularly outside Vitamin K anticoagulation; and combinations thereof.

Efficacy

A blood coagulation factor replacement product of the invention is characterized in that it exhibits an adequate efficacy. The efficacy of the product is preferably comparable to an efficacy of a reference blood coagulation factor replacement product having a molar ratio between ATIII to Factor II below 1:30. Preferably, "comparable" means in this context that the efficacy is identical to or better than said reference product or merely moderately reduced compared to said reference product. The molar ratio between ATIII to Factor II of below 1:30 of a reference treatment or reference product includes a treatment or product having no ATIII at all.

Efficacy in terms of present invention may be in particular quantified or expressed by an amount of blood loss, preferably by a certain reduction of the amount of blood loss.

Efficacy in terms of present invention according to a further aspect may be quantified or expressed by a value of time to hemostasis, preferably by a certain reduction of the value of time to hemostasis.

Efficacy in terms of present invention according to a further aspect may be quantified or expressed by a value of probability of survival following injury.

The amount of blood loss of the patient following the treatment with the product is decreased compared to an amount of blood loss following a placebo treatment or without treatment, wherein the amount of blood loss is preferably reduced to an amount of below 75%, below 70%, below 60%, below 55%, below 50%, below 45%, below 40% or below 35% of the amount following placebo treatment or of the amount without treatment. Hence, the efficacy of the product of the invention is adequate or even improved compared to said reference.

The amount of blood loss of the patient following the treatment with the product is either essentially identical or only moderately increased when compared to a reference treatment, or wherein the amount of blood loss of the patient following the treatment with the product is decreased when compared to a reference treatment, preferably, the amount of blood loss of the patient following the treatment with the product being decreased when compared to a reference treatment by at least 5%, at least 10%, at least 15% or at least 20%. Said reference treatment is identical to said treatment, except that the molar ratio between ATIII to Factor II of the product used in said reference treatment is below 1:30. Hence, the efficacy of the product of the invention is adequate or even improved compared to said reference.

In case of the amount of blood loss of the patient following the treatment with the product being only moderately increased when compared to an amount of blood loss of a reference treatment, said moderate increase amounting to not more than 60%, not more than 50%, not more than 40%, not more than 30%, not more than 20%, not more than 15%, not more than 10% or not more than 5%, wherein said reference treatment is identical to said treatment, except that the molar ratio between ATIII to Factor II of the product used in said reference treatment is below 1:30.

Preferably, the value of time to hemostasis of the patient following the treatment with the product is decreased compared to the value of time to hemostasis following placebo treatment or without treatment, wherein said value of time to hemostasis following treatment with the product is preferably decreased by at least 25%, at least 30%, at least 35%, at least 40%, at least 45%, at least 50%, at least 55% or at least 60% compared of the value following placebo treatment or of the value without treatment. Hence, the efficacy of the product of the invention is at least adequate when compared to said reference or even improved.

Further preferred, the value of time to hemostasis of the patient following the treatment with the product is either essentially identical or only moderately increased when compared to a reference treatment, or wherein the value of time to hemostasis of the patient following the treatment with the product is decreased when compared to a reference treatment, preferably, the value of time to hemostasis of the patient following the treatment with the product being decreased compared to a value following a reference treatment by at least 5%, by at least 10%, by at least 15% or by at least 20%, wherein said reference treatment is identical to said treatment, except that the molar ratio between ATIII to Factor II of the product used in said reference treatment is below 1:30. Hence, the efficacy of the product of the invention is at least adequate when compared to said reference or even improved.

In case of the value of time to hemostasis of the patient following the treatment with the product being only moderately increased when compared to a reference treatment, said moderate increase of the value amounting to not more than 80%, not more than 70%, not more than 60%, not more than 50%, not more than 40%, not more than 30%, not more than 20% or not more than 10%, wherein said reference treatment is identical to said treatment, except that the molar ratio between ATIII to Factor II of the product used in said reference treatment is below 1:30.

The patient's probability of survival following the treatment with the product of the invention is preferably substantially identical to the probability of survival following a reference treatment. Said reference treatment is identical to said treatment, except that the molar ratio between ATIII to Factor II of the product used in said reference treatment is below 1:30. Preferably, patient's probability of survival following the treatment with the product of the invention is substantially 100%.

Safety

A blood coagulation factor replacement product of the invention or a method of treatment according to the invention is characterized in that it exhibits an improved safety, i.e. the patient's risk for a thromboembolic complication is reduced.

Safety of the product or treatment of the invention is particularly improved when compared to the safety of a reference product or a reference treatment, the reference product or reference treatment being identical to said product or treatment, except that the molar ratio between ATIII to Factor II is below 1:30.

Safety in terms of present invention may be in particular quantified or expressed by a value of thrombin generation, preferably by a certain reduction of the thrombin generation, in particular by a certain reduction of the value of the Endogenous Thrombin Potential (ETP).

Safety in terms of present invention may be in particular quantified or expressed by a value of D-Dimer concentration (DD), preferably by a certain reduction of the D-Dimer concentration.

Safety in terms of present invention may be further quantified or expressed by a value of the patient's blood fibrinogen concentration.

Preferably, the value of thrombin generation of the patient following the treatment with the product is reduced when compared to a value of thrombin generation of a reference treatment by at least 5%, by at least 10%, by at least 15%, by at least 20%, by at least 25%, by at least 30%, by at least 35%, by at least 40%, by at least 45% or by at least 50%, in particular at 1 hour, at 2 hours and/or at 3 hours following administration of the product, wherein said reference treatment is identical to said treatment, except that the molar ratio between ATIII to Factor II of the product used in said reference treatment is below 1:30. The thrombin generation is in particular expressed by a value of the Endogenous Thrombin Potential (ETP).

Preferably, the value of D-Dimer concentration (DD) of the patient following the treatment with the product of the invention is reduced compared to a reference treatment by a factor of at least 1.5, at least 2, at least 2.5, at least 3, at least 3.5, at least 4, at least 4.5, at least 5, at least 5.5, at least 6, at least 6.5, at least 7, at least 8, at least 9, or at least 10, wherein said reference treatment is identical to said treatment, except that the molar ratio between ATIII to Factor II of the product used in said reference treatment is below 1:30. Said DD reduction is preferably achieved at about 1 hour, about 2 hours, about 3 hours and/or about 4 hours following administration of the product of the invention.

Preferably, the value of the patient's blood fibrinogen concentration following the treatment with the product of the invention is increased compared to the blood fibrinogen concentration following a reference treatment by a factor of at least 1.5, at least 2, at least 3, at least 4, at least 5, at least 7.5, or at least 10, wherein said reference treatment is identical to said treatment, except that the molar ratio between ATIII to Factor II of the product used in said reference treatment is below 1:30. Further preferred is that the value of the patient's blood fibrinogen concentration following the treatment with the product of the invention is essentially identical to the blood fibrinogen concentration following a placebo treatment or no treatment.

According to a further aspect of the invention, in addition to the treatment of a patient with a product of the invention the patient is treated in advance, simultaneously or subsequently with a replacement product, such as cryoprecipitate, or with a fibrinogen concentrate, preferably the replacement product or the fibrinogen concentrate being administered at a fibrinogen amount in a range between 5 mg/kg and 150 mg/kg bodyweight, between 10 mg/kg and 100 mg/kg bodyweight, preferably between 20 mg/kg and 80 mg/kg bodyweight.

According to a further preferred aspect, the patient's probability of survival following a co-treatment of the product of the invention together with fibrinogen is higher than the probability of survival following a reference co-treatment. Said reference co-treatment is identical to said treatment, except that the molar ratio between ATIII to Factor II of the product used in said reference co-treatment is below 1:30. Preferably, patient's probability of survival following said co-treatment with the product of the invention together with fibrinogen is substantially 100%.

According to a further preferred aspect, the patient's pulmonary arterial pressure following a co-treatment of the product of the invention together with fibrinogen is preferably lower than the patient's pulmonary arterial pressure following a reference co-treatment. Said reference co-treatment is identical to said treatment, except that the molar ratio between ATIII to Factor II of the product used in said reference co-treatment is below 1:30. In particular, essentially no increase of the patient's pulmonary arterial pressure following a co-treatment of the product of the invention together with fibrinogen occurs.

According to a further preferred aspect, the value of prothrombin time (PT) and/or the value of activated partial thromboplastin time (aPTT) of the patient following the treatment with the product is decreased compared to the value of prothrombin time (PT) and/or the value of activated partial thromboplastin time (aPTT) of a reference treatment by a factor of at least 1.5, at least 2.0, at least 2.5, at least 3.0, at least 3.5, at least 4.0, at least 4.5, at least 5.0, at least 7, or at least 10, wherein said reference treatment is identical to said treatment, except that the molar ratio between ATIII to Factor II of the product used in said reference treatment is below 1:30. Said respective values of PT or aPTT are in particular present at 1 about hour, at 2 about hours, at about 3 hours and/or at about 4 hours following administration.

According to a further preferred aspect, the value of prothrombin time (PT) and/or the value of activated partial thromboplastin time (aPTT) of the patient following the treatment with the product is essentially identical and/or has a maximum deviation of said value when compared to the respective value of prothrombin time (PT) and/or the respective value of activated partial thromboplastin time (aPTT) following placebo treatment or without treatment, provided that said maximum deviation does not exceed a factor of 5.0, of 3.0, of 2.5, of 2.0, or of 1.5. Said respective values of PT or aPTT are in particular present at about 1 hour, at about 2 hours, at about 3 hours and/or at about 4 hours following administration.

According to a further preferred aspect, the value of prothrombin time (PT) and/or the value of activated partial thromboplastin time (aPTT) of the patient following the treatment with the product is essentially remaining constant, preferably over a time period of about 1 hour, at about 2 hours, at about 3 hours and/or at about 4 hours following administration. According to a further preferred aspect, the value of prothrombin time (PT) and/or the value of activated partial thromboplastin time (aPTT) of the patient following the treatment with the product is not varying by more than a factor 10, a factor 8, a factor 6, a factor 5, a factor 4, a factor 3, a factor 2.5, a factor 2, or a factor 1.5, preferably over a time period of about 1 hour, at about 2 hours, at about 3 hours and/or at about 4 hours following administration.

The surprising findings regarding PT and aPTT of the product of the invention are related to both safety and efficacy of the product, in particular to improved safety and efficacy of the product.

According to a further aspect, safety in terms of present invention may be quantified or expressed by a value of a thrombus score as a surrogate marker for the risk of thromboembolic events, preferably by a certain reduction of the thrombus score. Preferably, the value of thrombus score following the treatment with the product when used as a surrogate marker is reduced compared to a value of the thrombus score of a reference treatment by at least 0.5 points, by at least 1 point, by at least 1.5 points or by 2 points, wherein said reference treatment is identical to said treatment, except that the molar ratio between ATIII to Factor II of the product used in said reference treatment is below 1:30.

Pharmaceutical Compositions

Therapeutic formulations of the composition of coagulation factors and ATIII of the invention, i.e. a product of the invention, suitable in the methods described herein can be prepared for storage as lyophilized formulations or aqueous solutions by mixing the coagulation factors and, if co-formulated, ATIII having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed. Hence, the product of the invention is provided in particular as a lyophilized product or a storage stable liquid. Said optionally pharmaceutically-acceptable carriers, excipients or stabilizers may preferably be present provided that they are approved for use for treatment of animals or humans, preferably for treatment humans.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothio-glycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional optional miscellaneous excipients include bulking agents (e.g., starch), chelating agents (e.g., EDTA), antioxidants (e.g., ascorbic acid, methionine, vitamin E), and cosolvents.

The pharmaceutical composition is preferably formulated to be administered intravenously.

A pharmaceutical product comprising Antithrombin III (ATIII) for co-administration with a prothrombin (Factor II) comprising product as described herein is one aspect of present invention. According to another aspect a pharmaceutical product comprising prothrombin (Factor II) for co-administration with an Antithrombin III (ATIII) comprising product is provided herewith. A further aspect of the invention pertains to a method of (i) treatment or prophylaxis of bleedings of patients having an acquired coagulation factor deficiency or (ii) treatment or prophylaxis of bleedings of patients having a congenital deficiency of a coagulation factor; by administering a blood coagulation factor replacement product as described supra to said patient. In particular in case of the latter three aspects of the invention, ATIII and Factor II can be arranged for and/or provided for simultaneous use, for separate use or for sequential use.

"Simultaneous use" in the sense of the invention means that the composition comprising at least isolated coagulation factor FII as defined herein and the composition comprising isolated ATIII are mixed and then administered as a mixture to a patient.

"Separate use" in the sense of the invention means that the composition comprising at least isolated coagulation factor FII as described herein and the composition comprising isolated ATIII are administered both at the same time or separately one after the other, whereby the sequence of said administrations is not relevant.

"Sequential use" in the sense of the invention means than the composition comprising at least isolated coagulation factor FII as described herein and the composition comprising isolated ATIII are administered separately, whereby the sequence of said administration is not relevant, and whereby the time interval between both administrations is not more than 2 days, preferentially not more than 1 day, more preferentially not more than 4 hours and most preferentially not more than 1 hour.

The compositions typically are supplied as part of a sterile, pharmaceutical composition that includes a pharmaceutically acceptable carrier. This composition can be in any suitable form (depending upon the desired method of administering it to a patient).

Determination of the total number of doses and length of treatment with a composition of the invention is well within the capabilities of those skilled in the art. The dosage of the product of the invention to be administered depends on the body weight and/or extent of anticoagulation or coagulopathy present.

The degree of severity of the disorder may also be considered to determine the appropriate dosage of a product or composition of the invention.

Those skilled in the art will appreciate that the invention described herein is susceptible to variations and modifications other than those specifically described. It is to be understood that the invention includes all such variations and modifications which fall within the spirit and scope. The invention also includes all of the features, compositions, steps, and compounds referred to or indicated in this specification, individually or collectively and any and all combinations of any two or more of said features, compositions, steps, and compounds.

Certain embodiments of the invention will now be described with reference to the following examples which are intended for the purpose of illustration only and are not intended to limit the scope of the generality hereinbefore described.

Examples—Rabbit Model

Hemostatic Efficacy of PCC in a Rabbit Model of Hemodilution Mediated Bleeding and Tissue Injury
Material and Methods
Animals Female CHB rabbits 3-4 months old weighing 2.8-4.0 kg (Manfred Bauer, Neuenstein-Lohe, Germany) were housed one per cage in wire-steel cages at 21-23° C. and 50% relative humidity under a 12 h/12 h light-darkness cycle. The animals were provided tap water ad libitum and fed rabbit pellets (Deukanin®, Deutsche Tiernahrung Cremer GmbH & Co. KG, Duesseldorf, Germany). All animals received care in compliance with the European Convention on Animal Care, and the study was approved by the organizational Ethics Committee.
Haemodilution All treatments were conducted in anesthesized animals. Anesthesia was induced by a combination of ketamine and xylazine and maintained via inhalative isoflurane anesthesia. The animals were then intubated and placed on a ventilator (Heyer Access, Heyer Medical AG, Bad Ems, Germany).

Animals were subjected to hemodilution in phases by withdrawal of 30 mL·kg-1 blood and infusion of 30 mL·kg-1 hydroxyethyl starch (HES) 200/0.5 (Infukoll 6%, Schwarz Pharma AG, Mannheim, Germany) prewarmed to 37° C. from the carotid artery (FIG. 1). That procedure was repeated at 45 min. At 30 min, during the interval between the two cycles of blood withdrawal and HES infusion, the animals received 15 mL·kg-1 salvaged erythrocytes, prepared from withdrawn whole rabbit blood by centrifugation for 10 min at 800×g, washing in normal saline and resuspension in Ringer's lactate, administered into the external jugular vein.
Kidney Injury At 60 min after commencement of hemodilution, a standardized renal injury was inflicted in the form of a 15 mm long and 5 mm deep scalpel incision at the lateral kidney pole (FIG. 1).
Treatment Animals were randomly allocated to receive i.v. administrations of isotonic saline (placebo), PCC (Beriplex®/Kcentra®, CSL Behring GmbH, Marburg, Germany) at doses of 25 IU/kg, ATIII (Kybernin®, CSL Behring GmbH, Marburg, Germany) at a dose of 11.5 IU/kg or combination treatment of PCC 25 IU/kg plus 11.5 or 23 IU/kg ATIII immediately prior to kidney incision injury (FIG. 1). Experimental groups consisted of 6-7 rabbits each. The PCC used within all examples comprises, if not stated otherwise, a low level ATIII, i.e. exhibits a molar ratio between ATIII to Factor II being below 1:30. The PCC used within the examples for reference purpose, also referred to as "conventional PCC" or only "PCC", comprises a molar ratio between ATIII to Factor II of below 1:30. An elevated level of ATIII in accordance with the invention, i.e. a molar ratio between ATIII to Factor II of at least 1:30, is achieved by co-administration of respective additional amounts of ATIII, representing a "modified PCC" of the invention.

The activity level provided in IU of the PCC for administration is referring to the nominal factor IX content of the PCC. One International Unit (IU) of activity is equivalent to that quantity of the respective coagulation factor in one mL of normal human plasma. The PCCs used within the examples, both conventional and modified, exhibit a factor II content which is substantially identical to the factor IX content based on the activity level provided in IU. Thus, for example a combination treatment of 50 IU/kg conventional PCC together with 25 IU/kg ATIII will result in a molar ratio between ATIII to Factor II of about 1:1 administered. The low level of ATIII provided within the herewith used conventional PCC can be disregarded for calculation of the molar ratio between ATIII to Factor II in a modified PCC.

Figure 2:
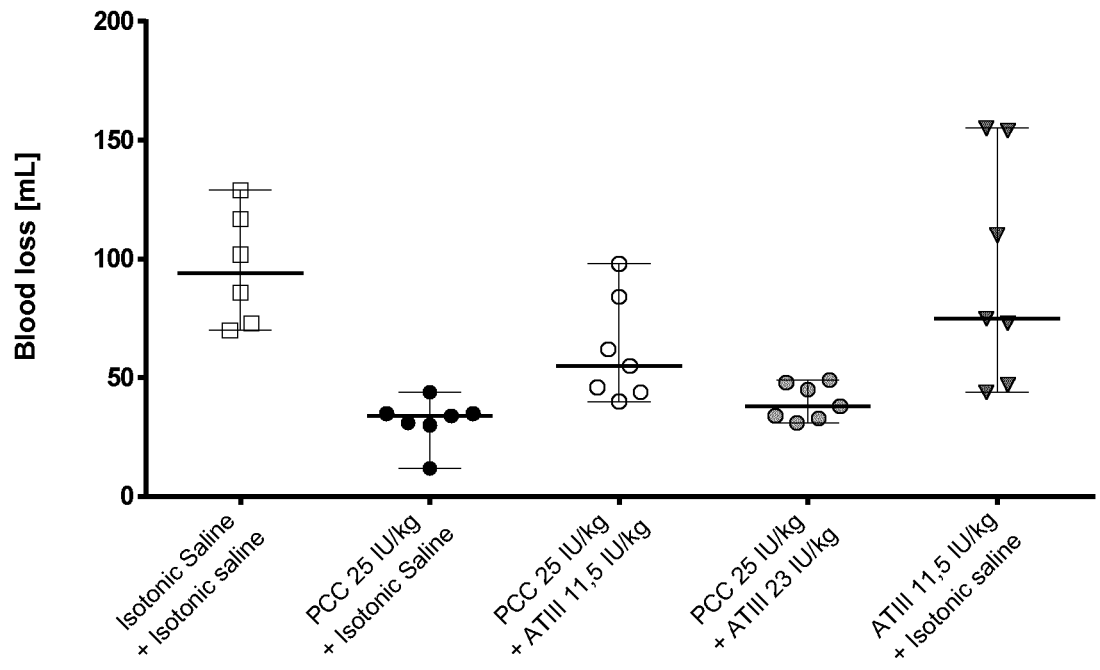
FIG. 2 shows the total blood loss following standardized kidney injury in hemodiluted rabbits following treatment with saline (placebo), PCC, ATIII or combination of PCC and ATIII. Data shown represent median with range. Abbreviations: PCC (prothrombin complex concentrate), ATIII (antithrombin III)

The PCCs used within the examples, both conventional and modified, exhibit a heparin content of about 1 IU/ml.
Endpoints The Study procedures for hemodilution, treatment, experimental kidney trauma and assessment of hemostatic effect are illustrated in FIG. 1 (Abbreviations: HES, hydroxyethyl starch; PCC (prothrombin complex concentrate), ATIII (antithrombin III)). The primary study endpoints were time to hemostasis and blood loss as observed up to 30 min following a standardized kidney incision injury (FIG. 1). Time to hemostasis was defined as the interval from the kidney incision until cessation of observable bleeding or oozing. Blood loss was the volume of blood collected from the incision site by suction. The 30 min observation period for blood loss and time to hemostasis began immediately after the incision.
Results Total blood loss following standardized kidney injury in hemodiluted rabbits following treatment with saline (placebo), PCC, ATIII or combination of PCC and ATIII is illustrated in FIG. 2. Data shown represent median with range. Abbreviations used are PCC (prothrombin complex concentrate) and ATIII (antithrombin III). As shown in FIG. 2, PCC at doses of 25 IU/kg was able to reduce total blood loss following standardized kidney injury from median of 94 mL (isotonic saline treatment; placebo) to 34 mL. The combination of PCC (25 IU/kg) and ATIII (11.5 or 23 IU/kg corresponding to molar ratios between ATIII to Factor II of about 1:1 and about 2:1, respectively) was also able to reduce total blood loss to median values of 55 and 38 mL, respectively. ATIII (11.5 IU/kg) alone did not have any relevant effects on blood loss.

Figure 3:
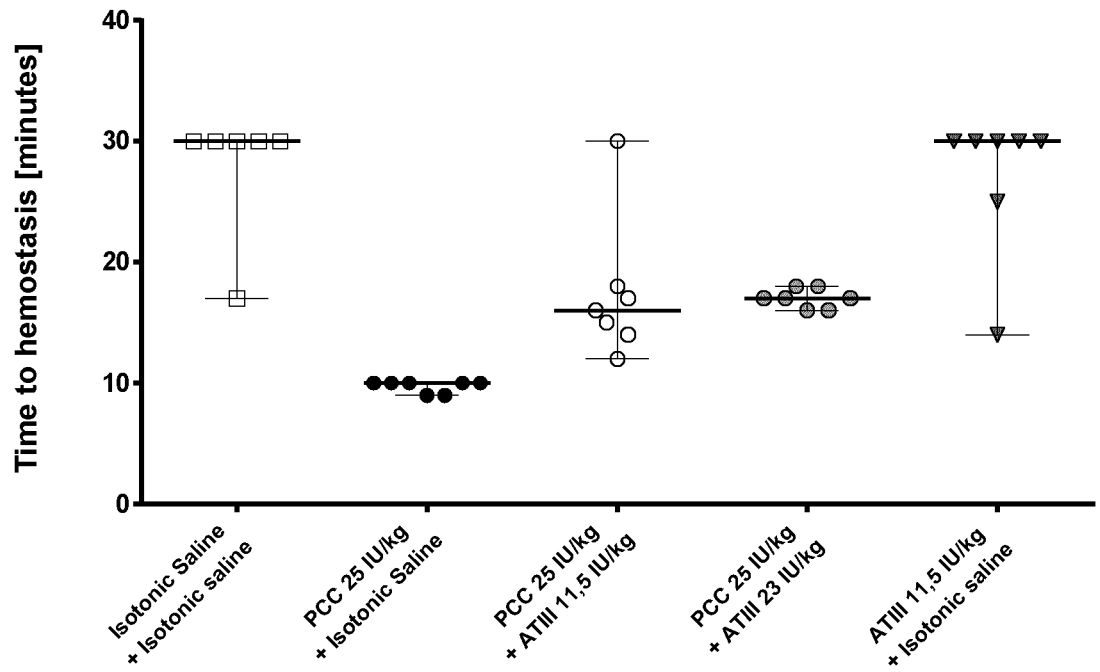
FIG. 3 shows the time to haemostasis following standardized kidney injury in hemodiluted rabbits following treatment with saline (placebo), PCC, ATIII or combination of PCC and ATIII. Data shown represent median with range. Abbreviations: PCC (prothrombin complex concentrate), ATIII (antithrombin III)

Time to haemostasis following standardized kidney injury in hemodiluted rabbits following treatment with saline (placebo), PCC, ATIII or combination of PCC and ATIII is illustrated in FIG. 3. Data shown represent median with range. Abbreviations used are PCC (prothrombin complex concentrate) and ATIII (antithrombin III). PCC at doses of 25 IU/kg was able to reduce the time to achieve hemostasis following standardized kidney injury from the maximum observation period of 30 min (isotonic saline treatment; placebo) to 10 min. The combination of PCC (25 IU/kg) and ATIII (11.5 or 23 IU/kg corresponding to molar ratios between ATIII to Factor II of about 1:1 and about 2:1, respectively) was also able to reduce time to hemostasis to median values of 16 and 17 min, respectively. ATIII (11.5 IU/kg) alone did not have any relevant effects on time to hemostasis (FIG. 3).

The Effects of ATIII Co-Administration on the Thrombogenicity of PCC in a Rabbit Model of Venous Stasis (Modified Wessler Model)

Material & Methods

Animals

Female New Zealand White rabbits 3-4 months old weighing 2.2-3.2 kg (Manfred Bauer, Neuenstein-Lohe, Germany), received care in compliance with the European Convention on Animal Care, and the study was approved by the local governmental authorities. The animals were housed individually in wire-steel cages at 21-23° C. and 50% relative humidity under a 12 h/12 h light-darkness cycle. The animals had free access to tap water and were fed rabbit pellets (Deukanin, Deutsche Tiernahrung Cremer GmbH & Co. KG, Duesseldorf, Germany) ad libitum. All animals received care in compliance with the European Convention on Animal Care, and the study was approved by the organizational Ethics Committee.

Treatment

Animals were randomly allocated to receive i.v. administrations of PCC (Beriplex®/Kcentra®, CSL Behring GmbH, Marburg, Germany) at doses of 300 IU/kg in combination with 7-138 IU/kg ATIII (Kybernin®, CSL Behring GmbH, Marburg, Germany)). Experimental groups consisted of 3 rabbits each. Animals treated with isotonica saline only (placebo) or 300 IU/kg PCC only served as control.

Modified Wessler Test

Procedures were performed under deep anesthesia (ketamine/xylazine). Venous stasis was induced 10 minutes after the end of infusion. Procoagulant effects were determined by exposing the contra lateral jugular vein and isolating a segment of approximately 2 cm, causing a complete stasis in the isolated segment. Thirty minutes after stasis induction the vein segment was excised and dissected in sodium citrate solution. Any observed thrombi were graded according to a scoring system from 0 to 3, and their wet weights were determined. Thrombus scores were defined as: 0 (no clot), 1 (one or a low number of small clots, too small to determine weights), 2 (not fully occluding clot, with measurable weight) or 3 (fully occluded clot).

Results

Figure 4A:
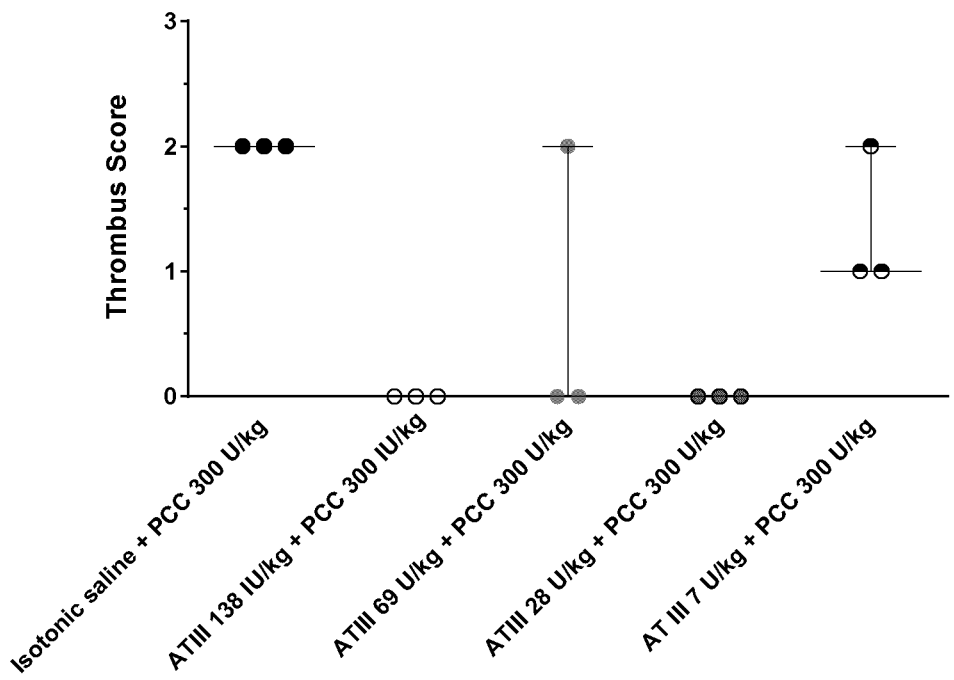
FIG. 4a shows the thrombus score following venous thrombosis in rabbits in the presence of treatment with saline (placebo), PCC or combination of PCC and ATIII. Data shown represent median with range. Abbreviations: PCC (prothrombin complex concentrate), ATIII (antithrombin III)

Thrombus score following venous thrombosis in rabbits in the presence of treatment with saline (placebo), PCC or combination of PCC and ATIII is illustrated in FIG. 4a. Data shown represent median with range. Abbreviations used are PCC (prothrombin complex concentrate) and ATIII (antithrombin III). As shown in FIG. 4a, PCC at doses of 300 IU/kg resulted in a thrombus score of 2 following 30 minutes of venous stasis which was fully inhibited by co-administration of ATIII at doses of 28 IU/kg, 69 IU/kg, and 138 IU/kg, corresponding to molar ratios between ATIII to Factor II of about 1:5, about 1:2, and about 1:1, respectively. Co-administration of ATIII at 7 IU/kg, corresponding to a molar ratio between ATIII to Factor II of about 1:20, resulted in partial reduction of thrombus formation with thrombus scores of 1-2.

Figure 4B:
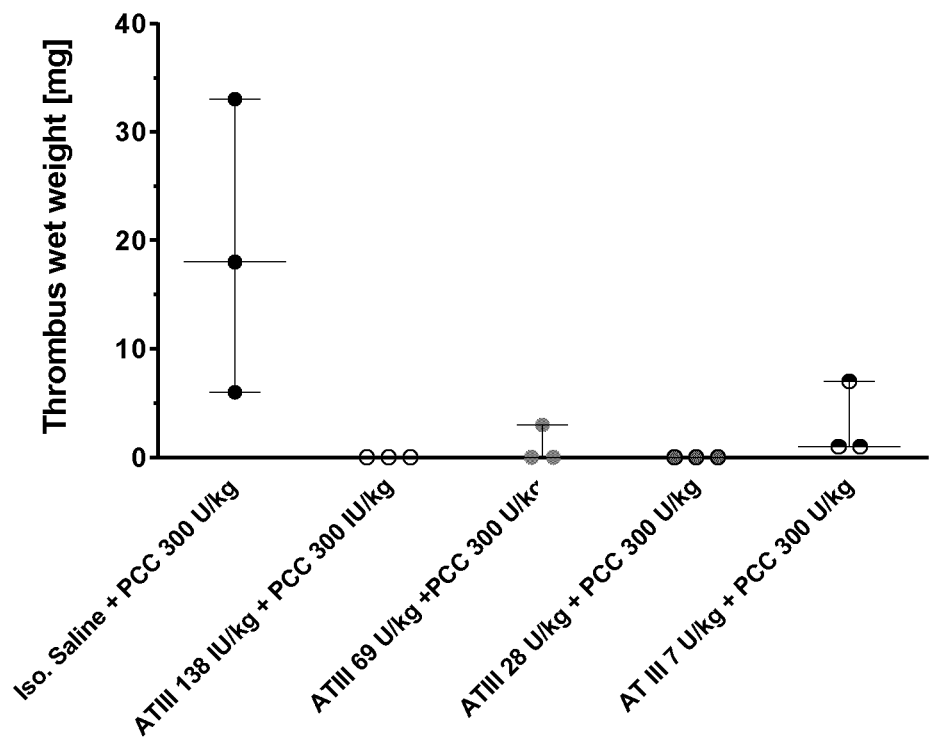
FIG. 4b shows the thrombus wet weight following venous thrombosis in rabbits in the presence of treatment with saline (placebo), PCC or combination of PCC and ATIII. Data shown represent median with range. Abbreviations: PCC (prothrombin complex concentrate), ATIII (antithrombin III)

Similarly, thrombus wet weight was reduced by co-administration of ATIII. Thrombus wet weight following venous thrombosis in rabbits in the presence of treatment with saline (placebo), PCC or combination of PCC and ATIII is illustrated in FIG. 4b. Data shown represent median with range. Abbreviations used are PCC (prothrombin complex concentrate) and ATIII (antithrombin III). As shown in FIG. 4b, PCC at doses of 300 IU/kg resulted in a thrombus wet weight of about 18 mg following 30 minutes of venous stasis which was fully reversed by co-administration of ATIII at doses of 28 IU/kg, 69 IU/kg, and 138 IU/kg, corresponding to molar ratios between ATIII to Factor II of about 1:5, about 1:2, and about 1:1, respectively. Co-administration of ATIII at 7 IU/kg, corresponding to a molar ratio between ATIII to Factor II of about 1:20, resulted in partial reduction of thrombus wet weight.

Examples—Pig Model

Material and Methods

Animals and Surgical Preparation

This study was conducted according to German legislation based on the Principles of Laboratory Animal Care. Official permission was granted from the appropriate governmental animal care and use office. German land race pigs from a disease-free breeding facility were housed in ventilated rooms for at least 5 days to acclimatize. They were fasted overnight before surgery, with water ad libitum.

Initial medication was administered by intramuscular injection: azaperone (4 mg kg$^{-1}$), and atropine (0.1 mg kg$^{-1}$). This was followed by anesthesia with propofol (3 mg kg$^{-1}$), administered by intravenous injection via an 18-G cannula into the right ear vein. Animals were ventilated in pressure-controlled mode at 20-22 breaths per minute with a tidal volume of 8 mL kg$^{-1}$, to keep $p_aCO_2$ between 36 and 40 mmHg with an oxygen fraction of 0.21 before trauma Cato, Draeger, Luebeck, Germany). Anesthesia was maintained with isoflurane at an endtidal concentration of 1.2-1.4% and constant infusion of fentanyl (2 µg kg$^{-1}$h$^{-1}$).

Initial fluid therapy comprised crystalloid solution (2 mL kg$^{-1}$ h$^{-1}$). Blood temperature; arterial, central venous and pulmonary arterial pressure; tail pulse oximetry and electrocardiography were monitored constantly, using a standard anesthesia monitor (AS/3, Datex Ohmeda, Helsinki, Finland).

Two 8.5-Fr catheters were implanted surgically in the right and left jugular veins for volume substitution, and a pulmonary artery catheter was placed in wedge-position through the right 8.5-Fr catheter. Hemodynamic variables were recorded through an 18-G catheter in the right arteria carotis communis. All blood samples were withdrawn from the arterial line.

Injury and Haemodilution

The first injury phase comprised 1.) bilateral closed femur fractures, 2.) an unilateral thorax contusion, both induced with captive bolt guns and 3. controlled withdrawal of about 60% of the animals estimated blood volume (65 ml/kg bodyweight) at a rate of 100 mL/min. Crystalloids were infused as required to maintain the mean arterial pressure (MAP) above 30 mmHg. After a hemorrhagic shock phase of approximately 20 min, volume losses were compensated for by crystalloid infusion and the inspiratory oxygen fraction was increased to 1.0. The second injury phase was induced by a standardized blunt liver. After the second injury phase, a second period of shock followed (10 min), just prior to the administration of haemostatic interventions.

Treatment

Ten minutes after the second trauma, animals were prospectively randomized using a computer-generated list in a 1:1:1:1 format using sealed envelopes into 1 of the following treatment groups:
1. Group 1: Control (Placebo)
2. Group 2: PCC50 IU/kg
3. Group 3: PCC50 IU/kg plus Antithrombin 50 IU/kg (PCC+AT50 group)
4. Group 4: PCC50 IU/kg plus Antithrombin 25 IU/kg (PCC+AT25 group)
5. Group 5: PCC50 IU/kg plus Antithrombin 12.5 IU/kg (PCC+AT12.5 group)
6. Group 6: PCC50 IU/kg plus Fibrinogen 80 mg/kg p (PCC+Fib group)
7. Group 7: PCC50 IU/kg plus Fibrinogen 80 mg/kg plus Antithrombin 50 IU/kg (PCC+Fib+AT50 group)

Thus, the following molar ratios between ATIII to Factor II have been tested: In group 2 (PCC50 IU/kg) the molar ratio between ATIII to Factor II was below 1:30 since a conventional PCC alone was administered. Group 2 (PCC50 IU/kg) is also referred to hereinafter as PCC monotherapy. In group 3 (PCC+AT50 group), group 4 (PCC+AT25 group) and group 5 (PCC+AT12.5 group) the molar ratio between ATIII to Factor II was about 1:0.5, about 1:1 and about 1:2, respectively. In group 6 (PCC+Fib group) the molar ratio between ATIII to Factor II was below 1:30. In group 7 (PCC+Fib+AT50 group) the molar ratio between ATIII to Factor II was about 1:0.5. ATIII, AT and antithrombin are used synonymously.

For PCC substation a four factor PCC (Beriplex® PN, CSL Behring, Germany) and Antithrombin (Kybernin® CSL Behring, Germany) was used. The observation period ended 240 minutes after the second injury. Animals surviving for the whole of this period were euthanized with pentobarbital. Immediately after death, the abdomen was reopened, the vena cava was clamped cranial to the liver, and the intraperitoneal blood was collected to determine the total blood loss post-injury. Several organs were removed post mortem and prepared for histologic examination.

Laboratory Analysis

Blood was collected and arterial blood gas analysis was performed at several time points after the second injury phase. For animals dying before 240 minutes post injury, the last assessment was performed immediately after death. The pH and partial pressures of oxygen and carbon dioxide, base excess and lactate were measured with a blood gas analyzer (ABL825, Radiometer GmbH, Willich, Germany). A standard hematology analyzer (MEK-6108, Nihon Kohden, Tokyo, Japan) was used to assess platelet count and hemoglobin concentration. Prothrombin time (PT), activated partial thromboplastin time (aPTT) and fibrinogen concentration, were determined by standard laboratory methods using the appropriate tests from Dade Behring (Dade Behring, Marburg, Germany) on a steel-ball coagulometer (MC 4 plus, Merlin Medical, Lemgo, Germany). D-Dimers were assessed with the appropriate test from Dade Behring (Dade Behring, Marburg, Germany).

Thromboelastometry and Thrombin Generation

Thrombin generation including the parameter endogenous thrombin potential (ETP) was measured in plasma using the Calibrated Automated Thrombogram (CAT, Thrombinoscope BV, Maastricht, The Netherlands) (Spronk H M, et al. Thromb Haemost. 2008; 100:362-364.). Assessments were conducted in 80 µL samples of plasma with 20 µL of fluorogenic substrate and 20 µL of trigger reagent. The trigger reagent was 1 pM tissue factor with 4 µM phospholipids. Each thrombin generation analysis was calibrated against the fluorescence curve obtained in the same plasma with a fixed amount of calibrator (Thrombin Calibrator, Thrombinoscope BV, Maastricht, The Netherlands). Fluorescence was measured using an Ascent Reader (Thermolabsystems OY, Helsinki, Finland), and thrombin generation curves were calculated using Thrombinoscope Version 4 software (Thrombinoscope BV, Maastricht, The Netherlands).

Pathologic Examination

After death, internal organs (heart, lungs, liver, and kidneys) were removed immediately and fixed in 10% buffered formalin. Injured parts of the liver were cut into 3-mm-thick slices and examined macroscopically and microscopically by a pathologist blinded to therapy to assess the degree of injury. In addition, representative tissue sections of all 4 organs were processed to determine the occurrence of thromboembolic events. All samples were embedded in paraffin and stained, both by H&E and by a standard elastica van Gieson protocol, for histologic examination under light microscopy. Both staining methods were applied to sections from all of the tissues.

Histologic examination confirmed beneficial effects of additional ATIII administration as described herein (data not shown).

Endpoints

The primary study endpoint of this study was the reduction of total blood loss following injury (efficacy) and the safety of the hemostatic intervention. Secondary endpoints included the impact on coagulation parameters.

Results

Figure 5:
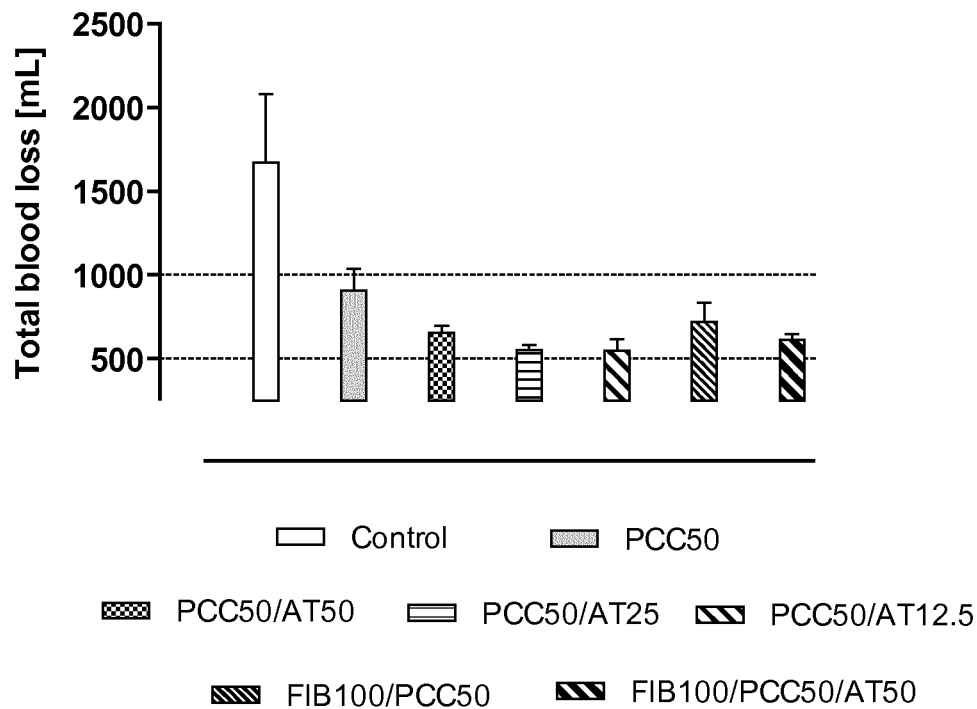
FIG. 5 shows total blood loss after the second liver injury in pigs. The combination of PCC and ATIII reduced blood loss compared with the control group and the monotherapy PCC50 treated group.

In FIG. 5 total blood loss after the second liver injury is illustrated. The combination of PCC and ATIII reduced blood loss compared with the control group and the monotherapy PCC50 treated group.

As shown in FIG. 5, total blood loss after the second injury phase, the primary endpoint of the study, was lower in the PCC plus antithrombin groups (PCC+AT50 group 653±42 mL; PCC+AT25 group 552±31 mL; PCC+AT12.5 group 548±68 mL) than in the monotherapy PCC 50 group (907±132 mL). Total blood loss in the PCC+Fib group (719±115 mL) was higher than in the PCC+Fib+AT50 group (613±34 mL). Total blood loss was highest in the control group (1671±409 mL; P<0.001 vs. all groups).

Figure 6:
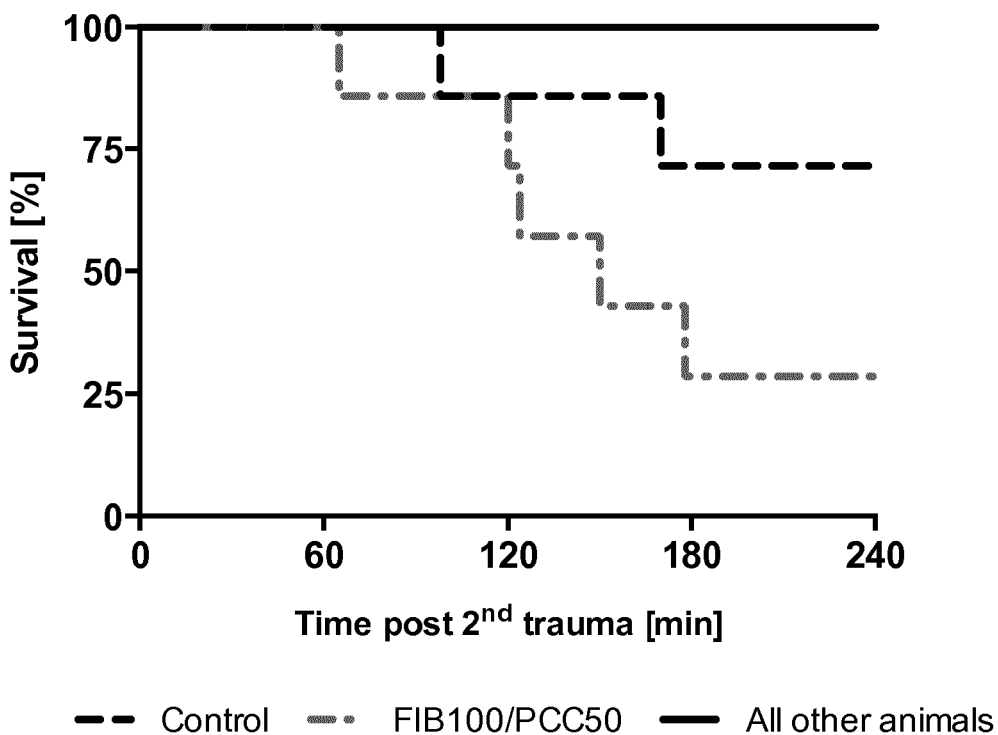
FIG. 6 shows pig data of survival presented as a Kaplan-Meier curve.

In FIG. 6 data of survival are presented as a Kaplan-Meier curve. All animals in the PCC monotherapy and PCC plus antithrombin groups survived (100%) the complete observational period, whereas 2 of 7 (29%) in the control group (mean survival time 210 min) died after the second trauma (FIG. 6).

Figure 7:
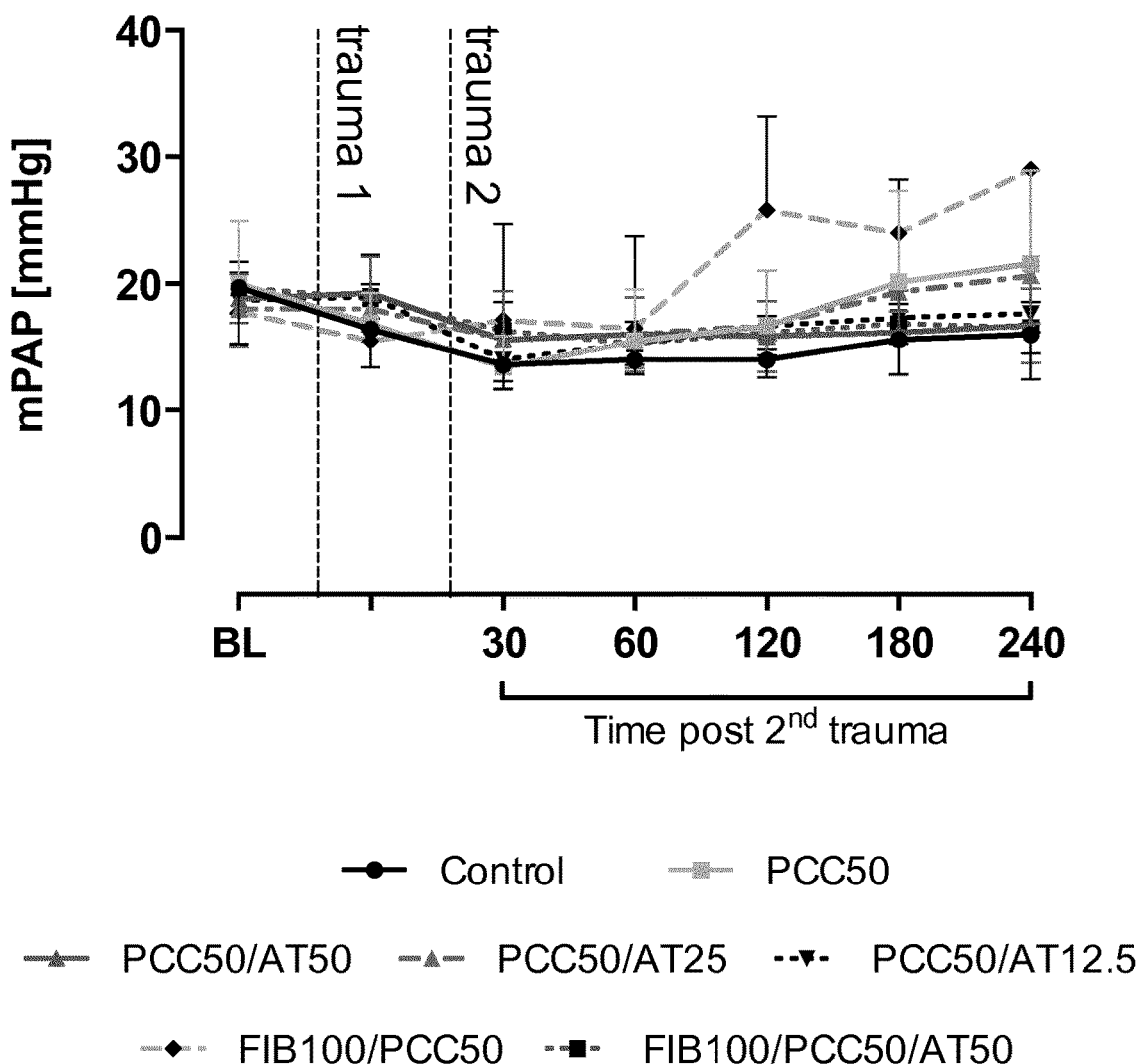
FIG. 7 shows pig data of the mean pulmonary pressure (MPAP, (mean±standard deviation)

According to the data presented in FIG. 6, 5 animals out of 7 animals (71%) in the PCC+Fib group died early (mean survival time 160 min) whereas all PCC+Fib+AT50 treated groups survived (100%). The early death from animals out of the PCC+Fib group was due to an increase in pulmonary arterial hypertension (26±7 mmHg at time point 120 min post second trauma). In FIG. 7 data of the mean pulmonary pressure (MPAP, (mean±standard deviation) are shown. No increase in pulmonary arterial pressure was observed in the PCC+Fib+AT50 group (e.g. 16±1 mmHg at time point 120 min post second trauma; FIG. 7).

Figure 8:
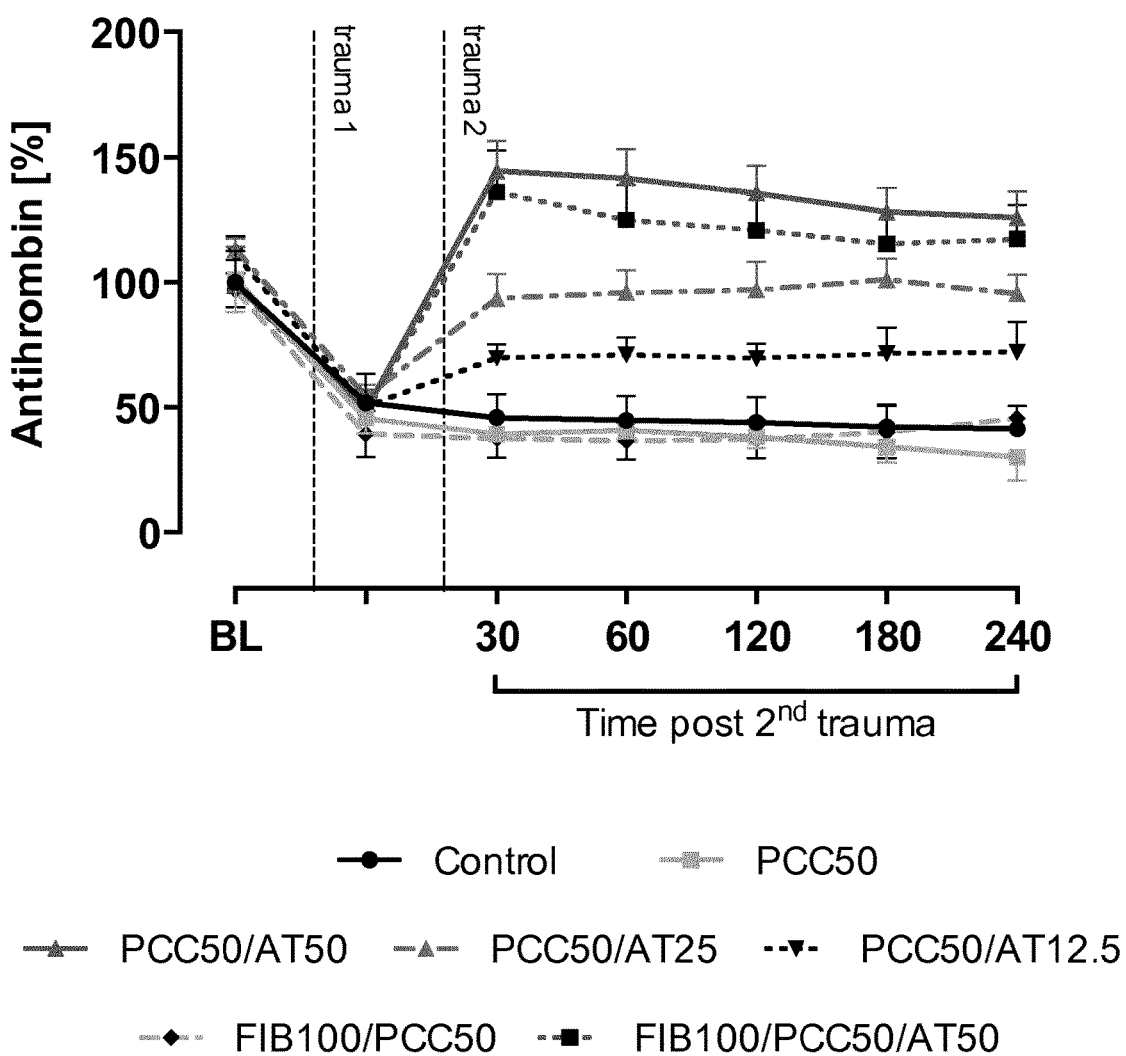
FIG. 8 shows antithrombin concentrations over the course of time after trauma and hemorrhagic shock in pigs (mean±standard deviation)

In FIG. 8 antithrombin concentrations over the course of time (mean±standard deviation) are illustrated. After trauma and hemorrhagic shock, antithrombin in all animals decreased to 48±9%. According to group allocation antithrombin substitution resulted in a dose-depended increase in antithrombin concentrations (30 min post second trauma: PCC+AT50 group 145±12%; PCC+AT25 group 94±10%; PCC+AT12.5 group 70±5%; PCC+Fib+AT50 136±17%) (FIG. 8). Antithrombin levels in these animals remained elevated over time. In non-antithrombin treated animals antithrombin remained at a level of 41±8% at 30 min post second trauma and at 37±11% at 240 min post second trauma.

Figure 9:
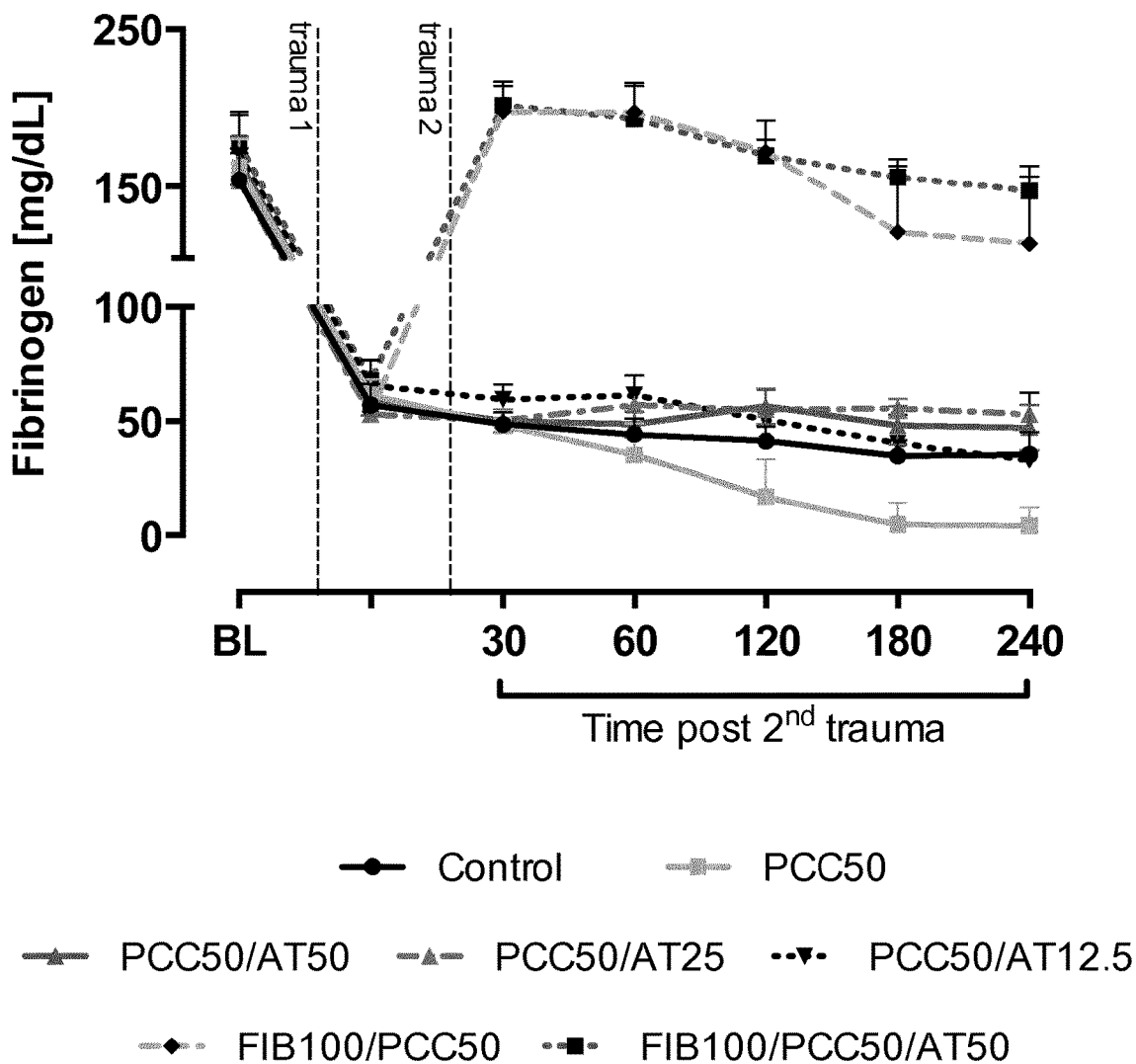
FIG. 9 shows fibrinogen concentrations over the course of time after trauma and hemorrhagic shock in pigs (mean±standard deviation)
Figure 10:
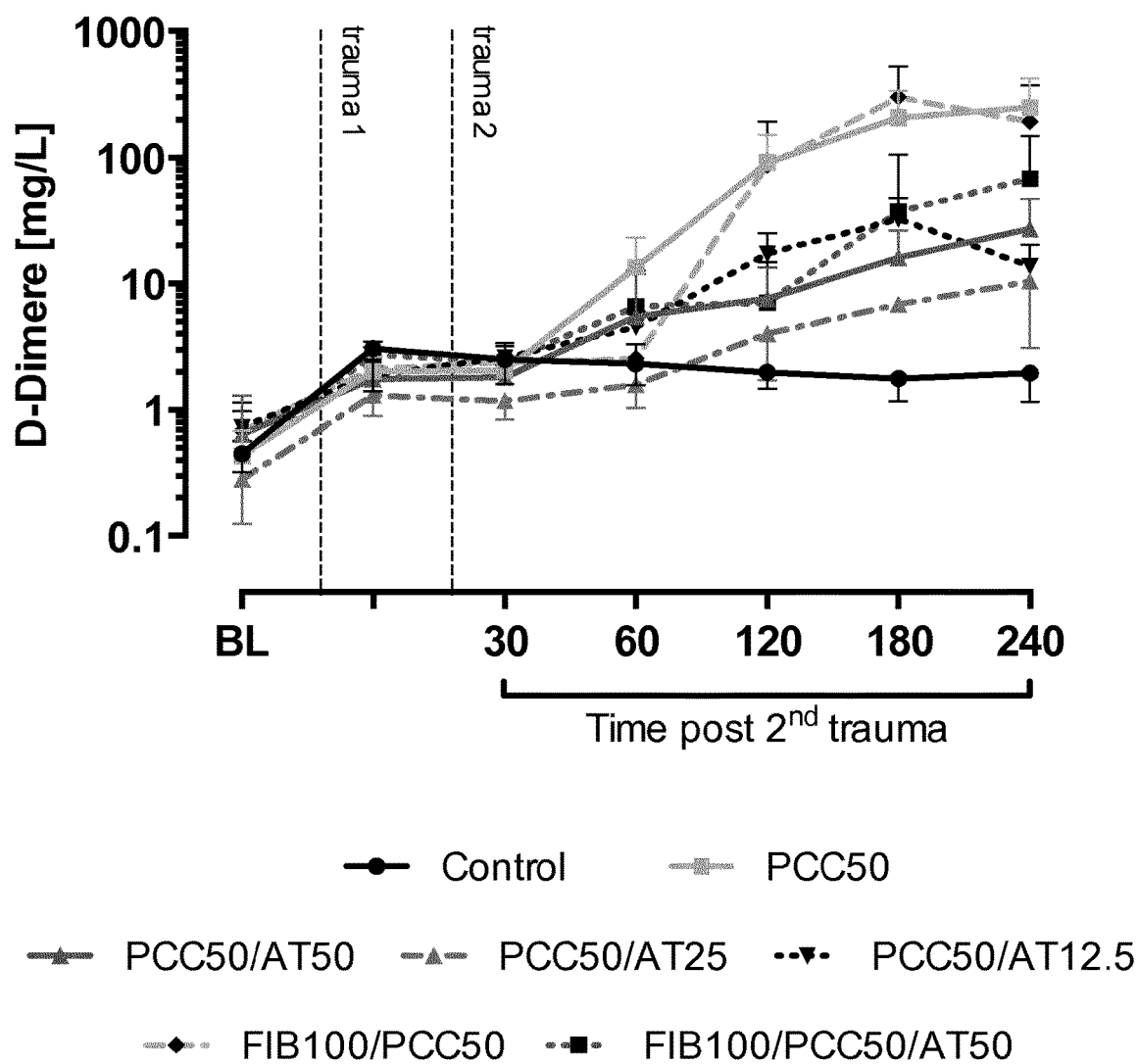
FIG. 10 shows D-Dimers over the course of time after trauma and hemorrhagic shock in pigs (mean±standard deviation)

In FIG. 9 fibrinogen concentrations over the course of time (mean±standard deviation) are shown. After trauma and hemorrhagic shock, fibrinogen concentrations in all animals decreased to 60±9 mg/dL. According to group allocation, fibrinogen substitution resulted in a dose-depended increase in fibrinogen concentrations (PCC+Fib group 198±16 mg/dL; PCC+Fib+AT50 group 202±15 mg/dL) (FIG. 9). Fibrinogen concentrations in PCC+Fib+AT50 remained stable over time. In PCC50 treated animals the concentration of fibrinogen decreased over time to 4±8 mg/dL and in PCC+Fib treated animals the concentration of fibrinogen decreased over time to 114±42 mg/dL at 240 min post second injury due to severe DIC. This consumption of fibrinogen was associated with a significant increase in D-dimers. In FIG. 10 concentration of D-Dimers over the course of time (mean±standard deviation) is presented. Immediately after PCC infusion, D-dimers had increased in the PCC50 and PCC+Fib group and these levels continued to increase throughout the observation period (240 min post second injury PCC50 group 249±176 mg/L; PCC+Fib group 193±180 mg/L). In the AT substituted groups D-dimers increased to a much lesser extent (240 min post second trauma: PCC+AT50 group 27±20 mg/L; PCC+AT25 group 10±7 mg/L; PCC+AT12.5 group 14±7 mg/L; PCC+Fib+AT50 group 68±79 mg/L).

Figure 11:
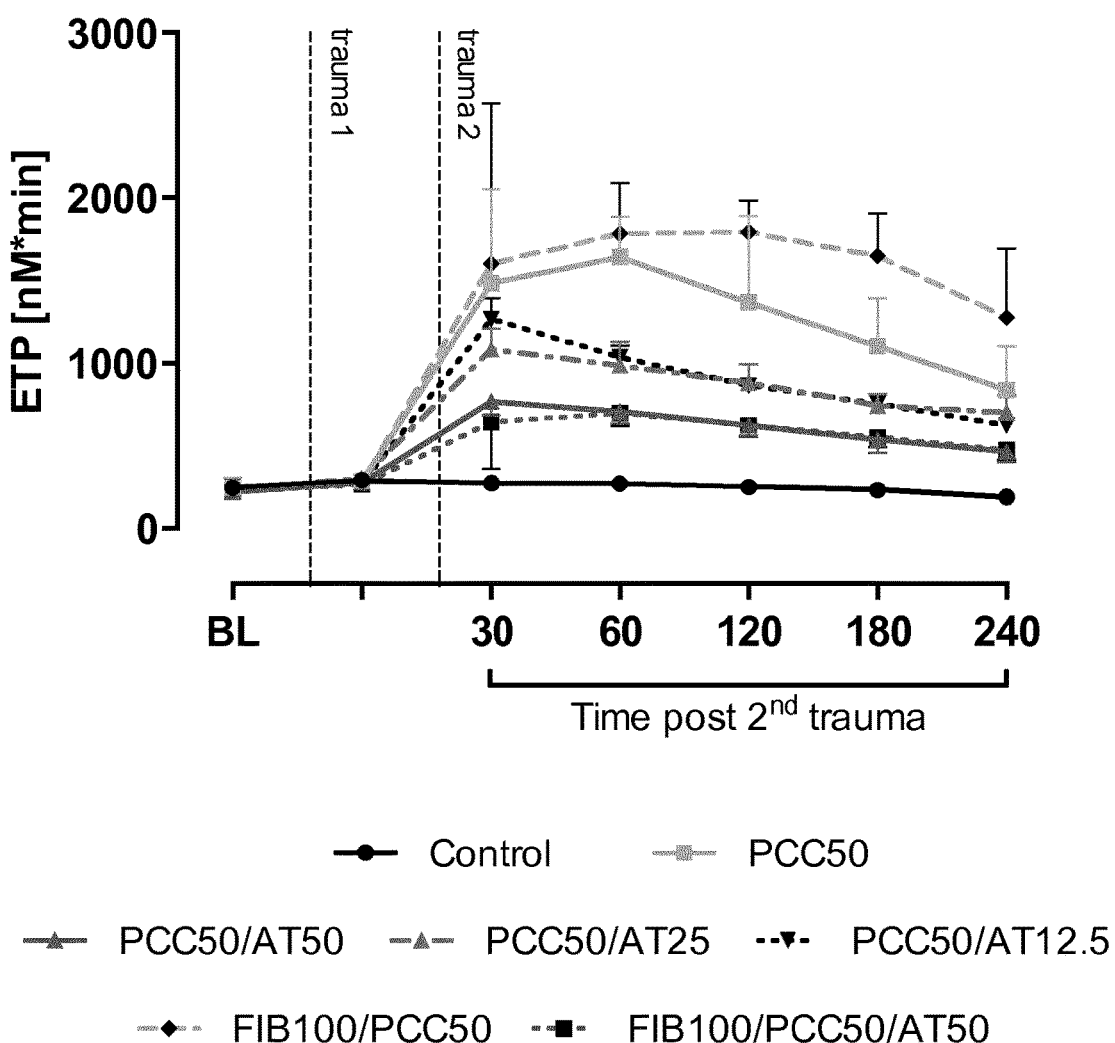
FIG. 11 shows thrombin generation over the course of time after trauma and hemorrhagic shock in pigs (mean±standard deviation)

FIG. 11 illustrates data regarding thrombin generation over the course of time (mean±standard deviation). Thrombin generation increased immediately after PCC administration in all animals receiving PCC (PCC50 group 1448±569 nM×min; PCC50+Fib group 1601±972 nM×min). The addition of antithrombin in animals from the PCC+Fib+AT50 (645±286 nM×min) and in the PCC plus antithrombin groups (PCC+AT50 group 769±84 nM×min; PCC+AT25 group 1084±123 nM×min; PCC+AT12.5 group 1266±126 nM×min) resulted in lower levels of thrombin generation. Thrombin generation in these animals was higher than in the controls (e.g. 30 min after the second trauma: 275±25 nM×min). Although thrombin generation gradually declined over time in PCC substituted animals during the observation period, thrombin generation remained higher than baseline at 240 minutes after second trauma.

Figure 12:
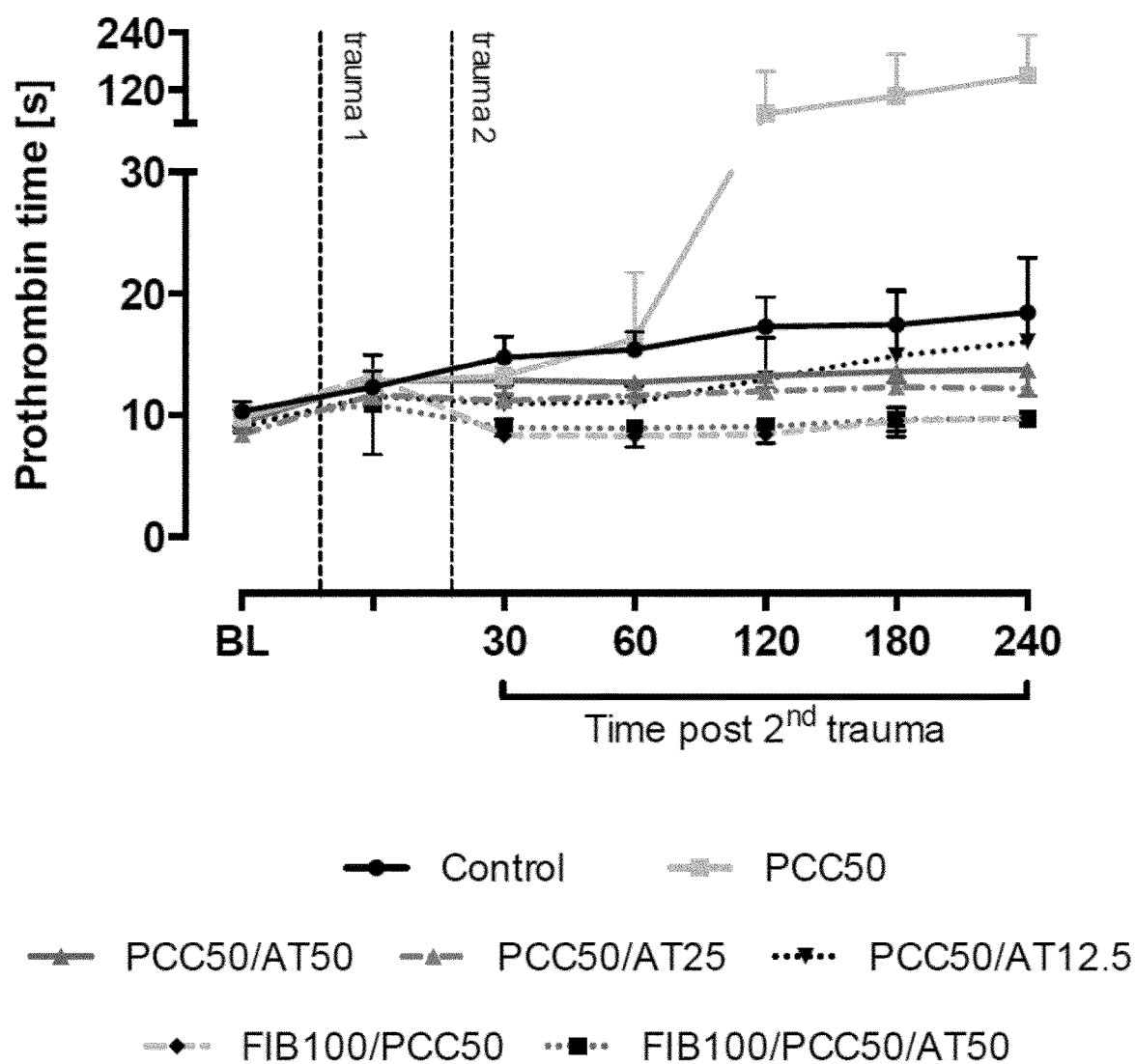
FIG. 12 shows the prothrombin time (PT) over the course of time after trauma and hemorrhagic shock in pigs (mean±standard deviation)

FIG. 12 illustrates data regarding prothrombin time (PT) over the course of time (mean±standard deviation). After second injury PT due to blood loss prolonged over time from 9.6±0.8 to sec. 12.3±2.0 sec. Animals receiving PCC 50 significantly prolonged after 60 min of the second injury up to 149±87 sec. at 240 min. The PT in all other intervention groups remained stable over time. Similarly findings were seen measuring the aPTT.

Figure 13:
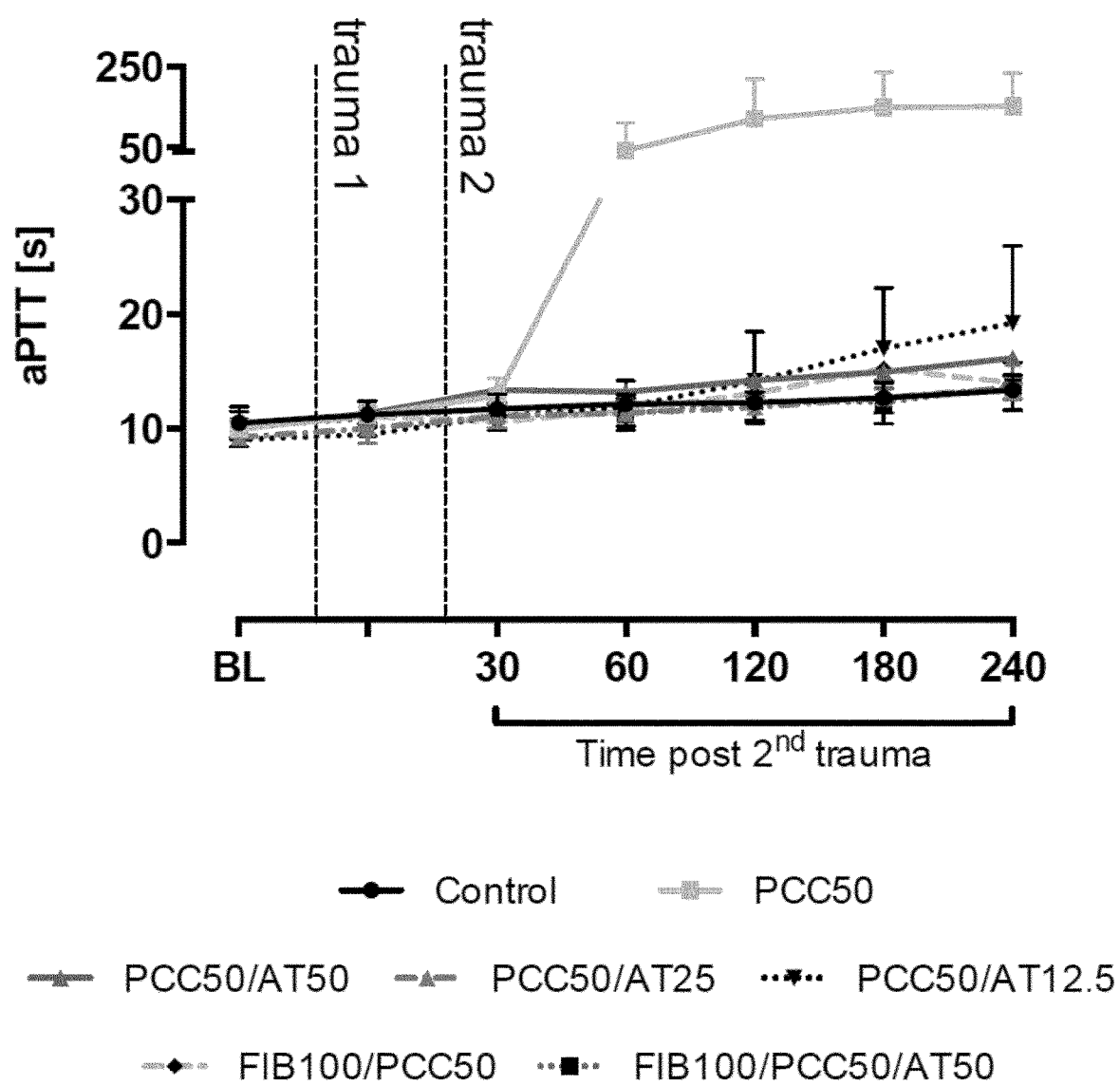
FIG. 13 shows the activated partial thromboplastin time (aPTT) over the course of time after trauma and hemorrhagic shock in pigs (mean±standard deviation).

FIG. 13 illustrates data regarding the activated partial thromboplastin time (aPTT) over the course of time (mean±standard deviation).

The invention claimed is:

1. A method for treatment or prophylaxis of bleeding in a patient having (i) an acquired coagulation factor deficiency or (ii) a congenital deficiency of a coagulation factor, comprising administering to the patient an effective amount of at least (a) an isolated prothrombin (Factor II), and (b) an isolated Antithrombin III (ATIII), wherein the molar ratio of the ATIII to the Factor II is at least 1:30, and wherein upon administration of (a) and (b), the patient's risk for a thromboembolic complication is reduced.

2. The method according to claim 1, wherein upon administration of (a) and (b), the patient's risk for a thromboembolic complication is reduced compared to a reference treatment in which the molar ratio of the ATIII to the Factor II is below 1:30.

3. The method according to claim 1, further comprising administering at least one isolated coagulation factor selected from the group consisting of Factor IX, Factor X, and Factor VII.

4. The method according to claim 1, wherein the value of prothrombin time (PT) and/or the value of activated partial thromboplastin time (aPTT) in the patient following the administration of (a) and (b) is decreased by a factor of at least 1.5 when compared to the corresponding value of PT or aPTT following a reference treatment in which the molar ratio of the ATIII to the Factor II is below 1:30.

5. The method according to claim 1, wherein the value of prothrombin time (PT) and/or the value of activated partial thromboplastin time (aPTT) in the patient following administration of (a) and (b) is essentially identical and/or has a maximum deviation that does not exceed a factor of 5.0 of the corresponding value of PT or aPTT following a placebo treatment or without treatment.

6. The method according to claim 1, further comprising administering heparin and/or albumin.

7. The method according to claim 1, wherein the Factor II is provided in a form having an activity level of between 10 and 80 IU/mL.

8. The method according to claim 1, wherein the molar ratio of the ATIII to the Factor II is no higher than 1:0.5.

9. The method according to claim 8, wherein the molar ratio of the ATIII to the Factor II is at least 1:25.

10. The method according to claim 1, wherein said treatment or prophylaxis comprises treatment and perioperative prophylaxis of bleeding in acquired deficiency of one or more prothrombin complex coagulation factors, in particular a deficiency caused by treatment with vitamin K antagonists, or in case of overdose of vitamin K antagonists, when rapid correction of the deficiency is required; or wherein said treatment or prophylaxis comprises treatment and perioperative prophylaxis of bleeding in congenital deficiency of any vitamin K dependent coagulation factors, in particular, when purified specific coagulation factors are not available.

11. The method according to claim 1, wherein in addition to the administration of (a) and (b), the patient is pre-treated, simultaneously treated, or subsequently treated with a fibrinogen replacement product or with a fibrinogen concentrate, wherein the replacement product or the fibrinogen concentrate is administered at a fibrinogen amount from 5 mg/kg to 150 mg/kg bodyweight.

12. The method according to claim 3, wherein (a) comprises a prothrombin complex concentrate (PCC) of either one of the following two types:
- a 3-factor complex comprising Factor II, Factor IX, and Factor X, or
- a 4-factor complex comprising Factor II, Factor IX, Factor X, and Factor VII.

13. A method for treatment or prophylaxis of bleeding in a patient having (i) an acquired coagulation factor deficiency or (ii) a congenital deficiency of a coagulation factor, comprising administering to the patient an effective amount of (a) a prothrombin complex concentrate (PCC), and (b) an Antithrombin III (ATIII), wherein the PCC comprises at least prothrombin (Factor II), Factor IX, and Factor X, provided that the molar ratio of the ATIII to the Factor II is at least 1:30, and wherein upon administration of (a) and (b) the patient's risk for a thromboembolic complication is reduced.

14. The method according to claim 1, wherein the ATIII and the Factor II are administered simultaneously.

15. The method according to claim 1, wherein the ATIII and the Factor II are administered sequentially.

16. The method according to claim 1, wherein the ATIII and the Factor II are administered separately.

\* \* \* \* \*